US008603777B1

(12) United States Patent
Hagen et al.

(10) Patent No.: US 8,603,777 B1
(45) Date of Patent: Dec. 10, 2013

(54) EXPRESSION OF FACTOR VII AND IX ACTIVITIES IN MAMMALIAN CELLS

(75) Inventors: Frederick S. Hagen, King County, WA (US); Mark J. Murray, King County, WA (US); Sharon J. Busby, King County, WA (US); Kathleen L. Berkner, King County, WA (US); Margaret Y. Insley, King County, WA (US); Richard G. Woodbury, King County, WA (US); Charles L. Gray, King County, WA (US)

(73) Assignee: ZymoGenetrics, Inc., Seattle, WA (US)

( * ) Notice: Subject to any disclaimer, the term of this patent is extended or adjusted under 35 U.S.C. 154(b) by 0 days.

(21) Appl. No.: 07/765,452

(22) Filed: Sep. 25, 1991

Related U.S. Application Data

(63) Continuation of application No. 06/724,311, filed on Apr. 17, 1985, now abandoned.

(51) Int. Cl.
*C12P 21/02* (2006.01)
*C12N 5/10* (2006.01)

(52) U.S. Cl.
USPC ............................ 435/69.6; 435/350; 435/352

(58) Field of Classification Search
USPC .......... 536/27; 435/68, 172.3, 240, 317, 69.1, 435/91, 172.1, 240.2, 252.3, 320.1; 530/384; 935/32, 47, 48, 55, 60, 70, 6, 935/9, 22, 27, 33
See application file for complete search history.

(56) References Cited

U.S. PATENT DOCUMENTS 4,382,083 A    5/1983  Thomas
4,399,216 A  *  8/1983  Axel et al. .................. 435/172.3
4,456,591 A    6/1984  Thomas
4,459,288 A    7/1984  Thomas
4,784,950 A  * 11/1988  Hagen et al.

FOREIGN PATENT DOCUMENTS

GB         2215409        *  3/1984
WO    WO 2006/014899 A2  *  9/2006

OTHER PUBLICATIONS

Bloom Nature 303; 474-475 1983.*
Anson et al *Nature* 315: 683-685, 1985.*
Berkner et al *Nucleic Acids Research* 13(3) 841-857 1985.*
Jagadeeswaran, et al *Somatic Cell and Molecular Genetics* 10 (5) 465-473. 1984.*
Broze, G.J. and Majerus, P.W. 1980. Purification and properties of human coagulation factor VII J.Biol. Chem. 255 : 1272-1247.*
Richards et al., Cell. Mol. Life Sci. 53:790-802, 1997.*
Clotting Factor VIII Cloned, *Nature*, vol. 312, Nov. 22, 1984, p. 307 George G. Brownlee and CHarles Rizza.
Characterization of the Human Factor VIII Gene, J. Gitschier et al, *Nature*, vol. 312, Nov. 22, 1984, pp. 326-330.

(Continued)

*Primary Examiner* — Nancy T Vogel
(74) *Attorney, Agent, or Firm* — Steven W. Parmelee

(57) ABSTRACT

Methods are disclosed for producing proteins having biological activity for blood coagulation mediated by Factor VIIa or Factor IX. The proteins are produced by mammalian host cells which have been stably transfected with a DNA construct containing a nucleotide sequence which codes at least partially for either Factor VII or Factor IX. The nucleotide sequence comprises a first nucleotide sequence encoding a calcium binding domain, joined to a second nucleotide sequence positioned downstream of the first sequence. The second sequence encodes a catalytic domain for the serine protease activity of either Factor VIIa or Factor IX. The joined sequences code for proteins having substantially the same biological activity for blood coagulation as either Factor VIIa or Factor IX.

6 Claims, 13 Drawing Sheets

(56) References Cited

OTHER PUBLICATIONS

Expression of Active Human Factor VIII from Recombinant DNA Clones, William Wood et al., *Nature*, vol. 312, Nov. 22, 1984 pp. 330-337.

Use of Human Factor VIIa in the Treatment of Two Hemophilia A Patiest with High-Titer Inhibitors, Ulla Hedner et al., J. Clin. Invest., vol. 71, Jun. 1983, pp. 1836-1841.

The Occurrence of β-Hydroxyaspartic Acid in the Vitamin K—Dependent Blood Coagulation Zymogens, B. A. McMullen et al., *Biochemical and Biophysical Research Communications*, vol. 115, No. 1, 1983, pp. 8-14.

The Esterase Activity of Coagulation Factor VII, *Journal of Biological Chemistry*, vol. 253, No. 7, Apr. 10, 1978, pp. 2203-2209.

Structure of Human Factor VIII, Gordon A. Vehar, et al., *Nature*, vol. 312, Nov. 22, 1984, pp. 337-342.

Molecular Cloning of a cDNA encoding Human Antihaemophilic Factor, John J. Toole et al., *Nature*, vol. 312, Nov. 22, 1984, pp. 342-347.

Enzymological Aspects of Blood Coagulation, W. Kisiel et al., Behring Inst. Mitt., No. 73, 29-42 (1983).

Isolation and Characterization of a cDNA Coding for Human Factor IX, *Proc. Natl. Acad. Sci. USA*, vol. 79, Nov. 1982, K. Kurachi et al.

A comparison of Human Prothrombin, Factor IX (Christmas Factor), Factor X (Stuart Factor), and Protein S, Richard G. Di Scipio et al., *Biochemistry*, (1977), 16, pp. 698-706.

Cloning of Vitamin K-Dependent Clotting Factors, E. W. Davie et al., Calcium Binding Proteins, by B. de Bernard et al (ed) pp. 45-52, 1983 Elsevier Science Publishers.

Purification of Human Factor VII Utilizing O-(Diethylaminoethyl)—Sephadex and Sulfopropyl-Sephadex Chromatography, L. V. M. Rao et al., *Analytical Biochemistry*, 136, 357, 1984.

Isolation and Characterization of Human Factor $VII_a$, Walter Kisie et al, *Thrombosis Research* 22, 375-380, 1981.

Comparison of Amino Acid Sequence of Bovine Coagulation Factor IX (Christmas Factor) With that of Other Vitamin K-dependent Plasma Proteins, *Proc. Natl. Acad. Sci. USA*, vol. 76, No. 10, pp. 4990-4994.

Basic Mechanisms in Blood Coagulation, Earl W. Davie et al., *Ann. Rev. Biochem.* vol. 44 (1975) pp. 799-824.

Bioengineering of Blood Plasma Proteins, G. A. Vehar, S. J. Haematol, Suppl. 40, vol. 33, 1984, pp. 45-51.

Purification and Some Characteristics of the Human Coagulation Factor VII, R. Flengsrud, *Eur. J. Biochem.*, 98, 1979 pp. 455-464.

Molecular Cloning of the Gene for Human Anti-Haemophilic Factor IX, K. H. Choo et al., *Nature*, vol. 299, Sep. 9, 1982, pp. 178-180.

The Gene Structure of Human Anti-Haemophilic Factor IX, D. S. Anson et al., *The Embo Journal*, vol. 3, No. 5, pp. 1053-1060, 1984.

Purification and Properties of Human Coagulation Factor VII, George J. Broze, et al., The Journal of Biological Chemistry, vol. 255, No. 4, Feb. 25, 1980, pp. 1242-1247.

\* cited by examiner

```
EcoRIa                        24                          39                         54
GAATTCCGG TGC AGG ACG AAG CTG TTC TGG ATT TCT TAC AGT GAT GGG GAC CAG
         Arg Thr Lys Leu Phe Trp Ile Ser Tyr Ser Asp Gly Asp Gln 69                       84                       99
TGT GCC TCA AGT CCA TGC CAG AAT GGG GGC TCC TGC AAG GAC CAG CTC CAG TCC
Cys Ala Ser Ser Pro Cys Gln Asn Gly Gly Ser Cys Lys Asp Gln Leu Gln Ser 114                      129                     144                     159
TAT ATC TGC TTC TGC CTC CCT GCC TTC GAG GGC CGG AAC TGT GAG ACG CAC AAG
Tyr Ile Cys Phe Cys Leu Pro Ala Phe Glu Gly Arg Asn Cys Glu Thr His Lys 174                      189                     204             Pst Ia
GAT GAC CAG CTG ATC TGT GTG AAC GAG AAC GGC GGC TGT GAG CAG TAC TGC AGT
Asp Asp Gln Leu Ile Cys Val Asn Glu Asn Gly Gly Cys Glu Gln Tyr Cys Ser 219                      234                      249                      264
GAC CAC ACG GGC ACC AAG CGC TCC TGT CGG TGC CAC GAG GGG TAC TCT CTG CTG
Asp His Thr Gly Thr Lys Arg Ser Cys Arg Cys His Glu Gly Tyr Ser Leu Leu 279                      294                      309                      324
GCA GAC GGG GTG TCC TGC ACA CCC ACA GTT GAA TAT CCA TGT GGA AAA ATA CCT
Ala Asp Gly Val Ser Cys Thr Pro Thr Val Glu Tyr Pro Cys Gly Lys Ile Pro

Xba I            339                      354                      369
ATT CTA GAA AAA AGA AAT GCC AGC AAA CCC CAA GGC CTA ATT GTG GGG GGC AAG
Ile Leu Glu Lys Arg Asn Ala Ser Lys Pro Gln Gly Arg Ile Val Gly Gly Lys 384                      399                     414                      429
GTG TGC CCC AAA GGG GAG TGT CCA TGG CAG GTC CTG TTG TTG GTG AAT GGA GCT
Val Cys Pro Lys Gly Glu Cys Pro Trp Gln Val Leu Leu Leu Val Asn Gly Ala 444                      459                      474
CAG TTG TGT GGG GGG ACC CTG ATC AAC ACC ATC TGG GTG GTC TCC GCG GCC CAC
Gln Leu Cys Gly Gly Thr Leu Ile Asn Thr Ile Trp Val Val Ser Ala Ala His 489                      504                      519                      534
TGT TTC GAC AAA ATC AAG AAC TGG AGG AAC CTG ATC GCG GTG CTG GGC GAG CAC
Cys Phe Asp Lys Ile Lys Asn Trp Arg Asn Leu Ile Ala Val Leu Gly Glu His 549                      564                      579                      594
GAC CTC AGC GAG CAC GAC GGG GAT GAG CAG AGC CGG CGG GTG GCG CAG GTC ATC
Asp Leu Ser Glu His Asp Gly Asp Glu Gln Ser Arg Arg Val Ala Gln Val Ile

609      Sma I       624                      639
ATC CCC AGC ACG TAC GTC CCG GGC ACC ACC AAC CAC GAC ATC GCG CTG CTC CGC
Ile Pro Ser Thr Tyr Val Pro Gly Thr Thr Asn His Asp Ile Ala Leu Leu Arg 654                      669                      684                      699
CTG CAC CAG CCC GTG GTC CTC ACT GAC CAT GTG GTG CCC CTC TGC CTG CCC GAA
Leu His Gln Pro Val Val Leu Thr Asp His Val Val Pro Leu Cys Leu Pro Glu
```

FIG. 1

```
                        714                    729                    744
CGG ACG TTC TCT GAG AGG ACG CTG GCC TTC GTG CGC TTC TCA TTG GTC AGC GGC
Arg Thr Phe Ser Glu Arg Thr Leu Ala Phe Val Arg Phe Ser Leu Val Ser Gly 759                 774         Nar I    789                804
TGG GGC CAG CTG CTG GAC CGT GGC GCC ACG GCC CTG GAG CTC ATG GTC CTC AAC
Trp Gly Gln Leu Leu Asp Arg Gly Ala Thr Ala Leu Glu Leu Met Val Leu Asn 819                 834     Pst Ib   849                864
GTG CCC CGG CTC ATG ACC CAG GAC TGC CTG CAG CAG TCA CGG AAG GTG GGA GAC
Val Pro Arg Leu Met Thr Gln Asp Cys Leu Gln Gln Ser Arg Lys Val Gly Asp 879                    894                909
TCC CCA AAT ATC ACG GAG TAC ATG TTC TGT GCC GGC TAC TCG GAT GGC AGC AAG
Ser Pro Asn Ile Thr Glu Tyr Met Phe Cys Ala Gly Tyr Ser Asp Gly Ser Lys 924                939                    954                969
GAC TCC TGC AAG GGG GAC AGT GGA GGC CCA CAT GCC ACC CAC TAC CGG GGC ACG
Asp Ser Cys Lys Gly Asp Ser Gly Gly Pro His Ala Thr His Tyr Arg Gly Thr 984                    999                1014
TGG TAC CTG ACG GGC ATC GTC AGC TGG GGC CAG GGC TGC GCA ACC GTG GGC CAC
Trp Tyr Leu Thr Gly Ile Val Ser Trp Gly Gln Gly Cys Ala Thr Val Gly His 1029            1044                    1059 TaqI        1074
TTT GGG GTG TAC ACC AGG GTC TCC CAG TAC ATC GAG TGG CTG CAA AAG CTC ATG
Phe Gly Val Tyr Thr Arg Val Ser Gln Tyr Ile Glu Trp Leu Gln Lys Leu Met 1089                1104                1119                    1138
CGC TCA GAG CCA CGC CCA GGA GTC CTC CTG CGA GCC CCA TTT CCC TAG CCCAGCAGCC
Arg Ser Glu Pro Arg Pro Gly Val Leu Leu Arg Ala Pro Phe Pro
                                                                    PstIc
    1148       1158       1168       1178       1188       1198    1208
CTGGCCTGTG GAGAGAAAGC CAAGGCTGCG TCGAACTGTC CTGGCACCAA ATCCCATATA TTCTTCTGCA 1218       1228       1238       1248       1258       1268       1278
GTTAATGGGG TAGAGGAGGG CATGGGAGGG AGGGAGAGGT GGGGAGGGAG ACAGAGACAG AAACAGAGAG 1288       1298       1308       1318       1328       1338       1348
AGACAGAGAC AGAGAGAGAC TGAGGGAGAG ACTCTGAGGA CCATGGACAG AGACTCAAAG AGACTCCAAG 1358       1368       1378       1388       1398       1408       1418
ATTCAAAGAG ACTAATAGAG ACACAGAGAT GGAATAGAAA AGATGAGAGG CAGAGGCAGA CAGGCGCTGG 1428       1438       1448       1458       1468       1478       1488
ACAGAGGGGC AGGGGAGTGC CAAGGTTGTC CTGGAGGCAG ACAGCCCAGC TGAGCCTCCT TACCTCCCTT
```

FIG. 1
(CONT.)

```
        1498       1508       1518       1528       1538       1548       1558
   CAGCCAAGCC CCACCTGCAC GTGATCTGCT GGCCCTCAGG CTGCTGCTCT GCCTTCATTG CTGGAGACAG 1568       1578       1588       1598       1608       1618       1628
   TAGAGGCATG ACACACATGG ATGCACACAC ACACACGCCA TGCACACACA CAGAGATATG CACACACACG 1638       1648       1658       1668       1678       1688       1698
   GATGCACACA CAGATGGTCA CACAGAGTAC GCAAACACAC CGATGCACAC GCACATAGAG ATATGCACAC 1708       1718       1728       1738       1748       1758       1768
   ACAGATGCAC ACACAGATAT ACACATGGAG TGCACGCACA TGCCAATGCA CGCACACATC AGTGCACACG 1778       1788       1798       1808       1818       1828       1838
   GATGCACAGA GATATGCACA CACCGATGTG CGCACACACA GATATGCACA CACATGGATG AGCACACACA 1848       1858       1868       1878       1888       1898       1908
   CACCAAGTGC GCACACACAC CGATGTACAC ACAGATGCAC ACACAGATGC ACACACACCG ATGCTGACTC 1918       1928       1938       1948       1958       1968       1978
   CATGTGTGCT GTCCTCTGAA GGCGGTTGTT TAGCTCTCAC TTTTCTGGTT CTTATCCATT ATCATCTTCA 1988       1998       2008       2018       2028       2038       2048
   CTTCAGACAA TTCAGAAGCA TCACCATGCA TGGTGGCGAA TGCCCCCAAA CTCTCCCCCA AATGTATTTC 2058       2068       2078       2088       2098       2108       2118
   TCCCTTCGCT GGGTGCCGGG CTGCACAGAC TATTCCCCAC CTGCTTCCCA GCTTCACAAT AAACGGCTGC 2128       2138       2148       2158       2168     EcoRIb
   GTCTCCTCGC AAAAAAAAAA AAAAAAAAAA AAAAAAAAAA AAAAAAAAAA AAGGAATTC
```

FIG. 1
(CONT.)

|  | 1 | 10 | 20 | 30 | 40 |
|---|---|---|---|---|---|
| FACTOR VII | ANA- | FLYYLRPCSL | YRYCKYYQCSF | YYARYIFYKKR | TKL |
| FACTOR IX | YNSG | KLYYFVQGNL | YRYCHYYKCSF | YYARYVFYNTY | RTY |
| FACTOR X | ANS- | FLYYHKKGHL | YRYCHYYYCSY | YYARYVFYDSD | KTNY |
| PROTEIN C | ANS- | FLYYLRHSSL | YRYCIYYICDF | YYALYIFQNVD | DYLA |
| PROTHROMBIN | ANT- | FLYYVRKGNL | YRYCVYYTCSY | YYAPYALYSST | ATDV |

|  | 50 | 60 | 70 |
|---|---|---|---|
| FACTOR VII | FWISYSDGDQCASS----- | -PCQNGGSCKDQLQSYICF |  |
| FACTOR IX | FWKQYVDGDQCESN----- | -PCLNGGSCKBDINSYECW |  |
| FACTOR X | FWNKYKDGDQCEYS----- | -PCQNQGKCKDGLGEYYCY |  |
| PROTEIN C | FWSKHVDGDQCLVLPLEHPCASLCCGHGYCIBGIGSFSCD |  |  |
| PROTHROMBIN | FWAKYYACEYARTPRDKLAACLEGNCAEGLGYNYRGRVNI |  |  |

|  | 80 | 90 | 100 | 110 |
|---|---|---|---|---|
| FACTOR VII | CLPAFEGRNCETHKDDQLICVNENGGCEEQYCSDHYCYKRSC |  |  |  |
| FACTOR IX | CPFGFEGKNCELDVT---- | -CNYKNGRCEQFCKNSADNKVVC |  |  |
| FACTOR X | CLEGFEGKNCELFTRKL-- | -CSLDNGDCDQFCKEEQNS-VVC |  |  |
| PROTEIN C | CRSGWEGRFCQREVSFLN- | -CSLDNGGCCTHYCLEEVGW-RRC |  |  |
| PROTHROMBIN | TRSGIECQLWRSRYPHKP-EINSTTHPGADLQENFCRNPDS |  |  |  |

|  | 120 | 130 | 140 |
|---|---|---|---|
| FACTOR VII | RCHEGYSLLADGVSCTPTVEYPCGKIPYLEKRNASKPQGR |  |  |
| FACTOR IX | SCTEGYRLAGNQKSCEPAVFPPCCGRVSVSQTSKLRT |  |  |
| FACTOR X | SCARGYTLADNGKACIPTGPYPCGKQTLER |  |  |
| PROTEIN C | SCAPGYKLCDDLLQCHPAVKFPCCRPAVKRMEKKRSHL |  |  |
| PROTHROMBIN | SNTGPWCYTTDPYVRRQECSIFVCGQDQVTVAMTPRS |  |  |

FIG. 2A

```
                              1                    10                   20                   30      36
From cDNA                     X X X X X X X X X X X X X X X X X X X X X X X X X X X X X X X X X X R T
                                                  * *                   * *     *               *
Amino Acid Sequence           A N A F L Y Y L R P G S L Y R Y C K Y Y Q C S F Y Y A R Y I F Y X X X X 40                   50                   60                   70
cDNA                          K L F W I S Y S D G D Q C A S S P C Q N G G S C K D Q L Q S Y I C F C L
                                *                                                               *
Amino Acid Sequence           L F W I S Y S D G D Q C A S S P C Q N G G S C K D Q L Q         I C F C L 80                   90                   100
cDNA                          P A F E G R N C E T H K D D Q L I C V N E N G G C E Q Y C S D H T G T K
                                                        *                                           *
Amino Acid Sequence           P A F E G R N C E T H K D D Q L                       C S D H T G T 110                  120                  130                  140
cDNA                          R S C R C H E G Y S L L A D G V S C T P T V E Y P C G K I P I L E K R M
                                *                                                               *
Amino Acid Sequence           S C R C H E G Y S L L A D G V S C T P T V E Y                       E K R ( )

150
cDNA                          A S K P Q G R
Amino Acid Sequence           A S K P Q G R
```

FIG. 2B

```
                            21                         36
GGATCC ATG CAG CGC GTG AAC ATG ATC ATG GCA GAA TCA CCA GGC
       MET Gln Arg Val Asn MET Ile MET Ala Glu Ser Pro Gly 66                         81
CTC ATC ACC ATC TGC CTT TTA GGA TAT CTA CTC AGT GCT GAA TGT
Leu Ile Thr Ile Cys Leu Leu Gly Tyr Leu Leu Ser Ala Glu Cys 96                         111                        126
ACA GTT TTT CTT GAT CAT GAA AAC GCC AAC AAA ATT CTG AAT CGG
Thr Val Phe Leu Asp His Glu Asn Ala Asn Lys Ile Leu Asn Arg 141                        156                        171
CCA AAG AGG TAT AAT TCA GGT AAA TTG GAA GAG TTT GTT CAA GGG
Pro Lys Arg Tyr Asn Ser Gly Lys Leu Glu Glu Phe Val Gln Gly 186                        201                        216
AAC CTT GAG AGA GAA TGT ATG GAA GAA AAG TGT AGT TTT GAA GAA
Asn Leu Glu Arg Glu Cys MET Glu Glu Lys Cys Ser Phe Glu Glu 231                        246                        261
GCA CGA GAA GTT TTT GAA AAC ACT GAA AGA ACA AAG CTG TTC TGG
Ala Arg Glu Val Phe Glu Asn Thr Glu Arg Thr Lys Leu Phe Trp 276                        291                        306
ATT TCT TAC AGT GAT GGG GAC CAG TGT GCC TCA AGT CCA TGC CAG
Ile Ser Tyr Ser Asp Gly Asp Gln Cys Ala Ser Ser Pro Cys Gln 321                        336                        351
AAT GGG GGC TCC TGC AAG GAC CAG CTC CAG TCC TAT ATC TGC TTC
Asn Gly Gly Ser Cys Lys Asp Gln Leu Gln Ser Tyr Ile Cys Phe 366                        381                        396
TGC CTC CCT GCC TTC GAG GGC CGG AAC TGT GAG ACG CAC AAG GAT
Cys Leu Pro Ala Phe Glu Gly Arg Asn Cys Glu Thr His Lys Asp 411                        426                        441
GAC CAG CTG ATC TGT GTG AAC GAG AAC GGC GGC TGT GAG CAG TAC
Asp Gln Leu Ile Cys Val Asn Glu Asn Gly Gly Cys Glu Gln Tyr 456                        471                        486
TGC AGT GAC CAC ACG GGC ACC AAG CGC TCC TGT CGG TGC CAC GAG
Cys Ser Asp His Thr Gly Thr Lys Arg Ser Cys Arg Cys His Glu 501                        516                        531
GGG TAC TCT CTG CTG GCA GAC GGG GTG TCC TGC ACA CCC ACA GTT
Gly Tyr Ser Leu Leu Ala Asp Gly Val Ser Cys Thr Pro Thr Val 546                        561                        576
GAA TAT CCA TCT GGA AAA ATA CCT ATT CTA GAA AAA AGA AAT GCC
Glu Tyr Pro Cys Gly Lys Ile Pro Ile Leu Glu Lys Arg Asn Ala 591                        606                        621
AGC AAA CCC CAA GGC CGA ATT GTG GGG GGC AAG GTG TGC CCC AAA
Ser Lys Pro Gln Gly Arg Ile Val Gly Gly Lys Val Cys Pro Lys
```

FIG. 7

```
          636                      651                      666
GGG GAG TGT CCA TGG CAG GTC CTG TTG TTG GTG AAT GGA GCT CAG
Gly Glu Cys Pro Trp Gln Val Leu Leu Leu Val Asn Gly Ala Gln 681                      696                      711
TTG TGT GGG GGG ACC CTG ATC AAC ACC ATC TGG GTG GTC TCC GCG
Leu Cys Gly Gly Thr Leu Ile Asn Thr Ile Trp Val Val Ser Ala 726                      741                      756
GCC CAC TGT TTC GAC AAA ATC AAG AAC TGG AGG AAC CTG ATC GCG
Ala His Cys Phe Asp Lys Ile Lys Asn Trp Arg Asn Leu Ile Ala 771                      786                      801
GTG CTG GGC GAG CAC GAC CTC AGC GAG CAC GAC GGG GAT GAG CAG
Val Leu Gly Glu His Asp Leu Ser Glu His Asp Gly Asp Glu Gln 816                      831                      846
AGC CGG CGG GTG GCG CAG GTC ATC ATC CCC AGC ACG TAC GTC CCG
Ser Arg Arg Val Ala Gln Val Ile Ile Pro Ser Thr Tyr Val Pro 861                      876                      891
GGC ACC ACC AAC CAC GAC ATC GCG CTG CTC CGC CTG CAC CAG CCC
Gly Thr Thr Asn His Asp Ile Ala Leu Leu Arg Leu His Gln Pro 906                      921                      936
GTG GTC CTC ACT GAC CAT GTG GTG CCC CTC TGC CTG CCC GAA CGG
Val Val Leu Thr Asp His Val Val Pro Leu Cys Leu Pro Glu Arg 951                      966                      981
ACG TTC TCT GAG AGG ACG CTG GCC TTC GTG CGC TTC TCA TTG GTC
Thr Phe Ser Glu Arg Thr Leu Ala Phe Val Arg Phe Ser Leu Val 996                     1011                     1026
AGC GGC TGG GGC CAG CTG CTG GAC CGT GGC GCC ACG GCC CTG GAG
Ser Gly Trp Gly Gln Leu Leu Asp Arg Gly Ala Thr Ala Leu Glu 1041                     1056                     1071
CTC ATG GTC CTC AAC GTG CCC CGG CTG ATG ACC CAG GAC TGC CTG
Leu MET Val Leu Asn Val Pro Arg Leu MET Thr Gln Asp Cys Leu 1086                     1101                     1116
CAG CAG TCA CGG AAG GTG GGA GAC TCC CCA AAT ATC ACG GAG TAC
Gln Gln Ser Arg Lys Val Gly Asp Ser Pro Asn Ile Thr Glu Tyr 1131                     1146                     1161
ATG TTC TGT GCC GGC TAC TCG GAT GGC AGC AAG GAC TCC TGC AAG
MET Phe Cys Ala Gly Tyr Ser Asp Gly Ser Lys Asp Ser Cys Lys 1176                     1191                     1206
GGG GAC AGT GGA GGC CCA CAT GCC ACC CAC TAC CGG GGC ACG TGG
Gly Asp Ser Gly Gly Pro His Ala Thr His Tyr Arg Gly Thr Trp 1221                     1236                     1251
TAC CTG ACG GGC ATC GTC AGC TGG GGC CAG GGC TGC GCA ACC GTG
Tyr Leu Thr gly Ile Val Ser Trp Gly Gln Gly Cys Ala Thr Val
```

FIG. 7
(CONT.)

```
      1266                 1281                 1296
GGC CAC TTT GGG GTG TAC ACC AGG GTC TCC CAG TAC ATC GAG TGG
Gly His Phe Gly Val Tyr Thr Arg Val Ser Gln Tyr Ile Glu Trp 1311                 1326                 1341
CTG CAA AAG CTC ATG CGC TCA GAG CCA CGC CCA GGA GTC CTC CTG
Leu Gln Lys Leu MET Arg Ser Glu Pro Arg Pro Gly Val Leu Leu 1356                         1378      1388      1398
CGA GCC CCA TTT CCC TAG CCCAGCAGCC CTGGCCTGTG GAGAGAAAGC
Arg Ala Pro Phe Pro 1408      1418      1428      1438      1448
CAAGGCTGCG TCGAACTGTC CTGGCACCAA ATCCCATATA TTCTTCTGCA 1458      1468      1478      1488      1498
GTTAATGGGG TAGAGGAGGG CATGGGAGGG AGGGAGAGGT GGGGAGGGAG 1508      1518      1528      1538      1548
ACAGAGACAG AAACAGAGAG AGACAGAGAC AGAGAGAGAC TGAGGGAGAG 1558      1568      1578      1588      1598
ACTCTGAGGA CCATGGAGAG AGACTCAAAG AGACTCCAAG ATTCAAAGAG 1608      1618      1628      1638      1648
ACTAATAGAG ACACAGAGAT GGAATAGAAA AGATGAGAGG CAGAGGCAGA 1658      1668      1678      1688      1698
CAGGCGCTGG ACAGAGGGGC AGGGGAGTGC CAAGGTTGTC CTGGAGGCAG 1708      1718      1728      1738      1748
ACAGCCCAGC TGAGCCTCCT TACCTCCCTT CAGCCAAGCC CCACCTGCAC 1758      1768      1778      1788      1798
GTGATCTGCT GGCCCTCAGG CTGCTGCTCT GCCTTCATTG CTGGAGACAG 1808      1818      1828      1838      1848
TAGAGGCATG ACACACATGG ATGCACACAC ACACACGCCA TGCACACACA 1858      1868      1878      1888      1898
CAGAGATATG CACACACACG GATGCACACA CAGATGGTCA CACAGAGTAC 1908      1918      1928      1938      1948
GCAAACACAC CGATGCACAC GCACATAGAG ATATGCACAC ACAGATGCAC
```

FIG. 7
(CONT.)

```
      1958       1968       1978       1988       1998
  ACACAGATAT ACACATGGAG TGCACGCACA TGCCAATGCA CGCACACATC 2008       2018       2028       2038       2048
  AGTGCACACG GATGCACAGA GATATGCACA CACCGATGTG CGCACACACA 2058       2068       2078       2088       2098
  GATATGCACA CACATGGATG AGCACACACA CACCAAGTGC GCACACACAC 2108       2118       2128       2138       2148
  CGATGTACAC ACAGATGCAC ACACAGATGC ACACACACCG ATGCTGACTC 2158       2168       2178       2188       2198
  CATGTGTGCT GTCCTCTGAA GGCGGTTGTT TAGCTCTCAC TTTTCTGGTT 2208       2218       2228       2238       2248
  CTTATCCATT ATCATCTTCA CTTCAGACAA TTCAGAAGCA TCACCATGCA 2258       2268       2278       2288       2298
  TGGTGGCGAA TGCCCCCAAA CTCTCCCCCA AATGTATTTC TCCCTTCGCT 2308       2318       2328       2338       2348
  GGGTGCCGGG CTGCACAGAC TATTCCCCAC CTGCTTCCCA GCTTCACAAT 2358       2368       2378       2388       2398
  AAACGGCTGC GTCTCCTCGC AAAAAAAAAA AAAAAAAAAA AAAAAAAAAA 2408       2418       2428       2438
  AAAAAAAAAA AAGGAATTCG AGCTCGGTAC CCGGGGATCC
```

FIG. 7
(CONT.)

EXPRESSION OF FACTOR VII AND IX ACTIVITIES IN MAMMALIAN CELLS

CROSS-REFERENCE TO RELATED APPLICATION

This application is a continuation of U.S. application Ser. No. 06/724,311, filed Apr. 17, 1985, now abandoned.

TECHNICAL FIELD

The present invention relates to blood coagulation factors in general, and more specifically, to the expression of proteins having biological activity for blood coagulation.

BACKGROUND ART

Blood coagulation is a process consisting of a complex interaction of various blood components or factors which eventually gives rise to a fibrin clot. Generally, the blood components which participate in what has been referred to as the coagulation "cascade" are proenzymes or zymogens, enzymatically inactive proteins which are converted to proteolytic enzymes by the action of an activator, itself an activated clotting factor. Coagulation factors which have undergone such a conversion are generally referred to as "activated factors," and are designated by the addition of a lower case postscript "a" (e.g., VIIa).

There are two separate systems which can promote blood clotting and thereby participate in normal haemostasis. These systems have been referred to as the intrinsic and the extrinsic coagulation pathways. The intrinsic pathway refers to those reactions which lead to thrombin formation through utilization of factors present only in plasma. An intermediate event in the intrinsic pathway is the activation of Factor IX to Factor IXa, a reaction catalyzed by Factor XIa and calcium ions. Factor IXa then participates in the activation of Factor X in the presence of Factor VIIIa, phospholipid and calcium ions. The extrinsic pathway involves plasma factors as well as components present in tissue extracts. Factor VII, one of the proenzymes referred to above, participates in the extrinsic pathway of blood coagulation by converting (upon its activation to VIIa) Factor X to Xa in the presence of tissue factor and calcium ions. Factor Xa in turn then converts prothrombin to thrombin in the presence of Factor Va, calcium ions and phospholipid. Because the activation of Factor X to Factor Xa is an event shared by both the intrinsic and extrinsic pathways, Factor VIIa can be used for the treatment of patients with deficiencies or inhibitors of Factor VIII (Thomas, U.S. Pat. No. 4,382,083). There is also some evidence to suggest that Factor VIIa may participate in the intrinsic pathway as well (Zur and Nemerson, *J. Biol. Chem.* 253: 2203-2209, 1978) by playing a role in the activation of Factor IX.

Experimental analysis has revealed that human Factor VII is a single-chain glycoprotein with a molecular weight of approximately 50,000 daltons. In this form, the factor circulates in the blood as an inactive zymogen. Activation of Factor VII to VIIa may be catalyzed by several different plasma proteases, such as Factor XIIa. Activation of Factor VII results in the formation of two polypeptide chains, a heavy chain ($M_r$=34,000) and a light chain ($M_r$=24,000), held together by at least one disulfide bond. Factor VII may also be activated to VIIa in vitro, for example, by the method disclosed by Thomas in U.S. Pat. No. 4,456,591.

Factor IX circulates in the blood as a single-chain precursor of molecular weight 57,000 and is converted to an active serine protease (Factor IXa) upon cleavage by Factor XIa in the presence of Factor VIII. Factor IXa consists of a light chain and a heavy chain of molecular weights 16,000 and 29,000, respectively.

Current treatment practices for patients having coagulation disorders (e.g., deficiencies of Factor VIII and IX) generally involve replacement therapy with cryoprecipitate or other fractions of human plasma containing enriched levels of a particular factor. These preparations have heretofore been obtained from pooled human plasma, although the preparation of cryoprecipitates requires the use of a relatively large amount of human plasma as starting material.

Therapeutic uses of Factor VII exist in the treatment of individuals exhibiting a deficiency in Factor VII, as well as Factor VIII and Factor IX deficient populations, and individuals with Von Willebrand's disease. More specifically, individuals receiving Factors VIII and IX in replacement therapy frequently develop antibodies to these proteins. Continuing treatment is exceedingly difficult because of the presence of these antibodies. Patients experiencing this problem are normally treated with an activated prothrombin complex known to consist of a mixture of active and inactive clotting enzymes, including Factor VIIa. Further, recent studies indicate that small amounts (40-50 micrograms) of injected Factor VIIa are effective in controlling serious on-going bleeding episodes in Factor VIII deficient patients who have high levels of antibody in their blood (Hedner and Kisiel, *J. Clin. Invest.* 71: 1836-1841, 1983).

Due to the diverse sources of the plasma used in the preparation of cryoprecipitates, it is difficult to test the preparations to ensure that they are free of viral contamination. For instance, essentially all recipients of cryoprecipitate show a positive test for hepatitis. Recent reports have also indicated that some hemophiliacs receiving cryoprecipitate have developed acquired immune deficiency syndrome (AIDS). In addition, the purification of large amounts of these factors is extremely difficult and expensive.

Consequently, there exists a need in the art for a method of producing relatively large quantities of pure preparations of Factors VIIa and Factor IX. The present invention fulfills this need through the use of recombinant DNA technology, successfully eliminating the problem of viral contamination and, at the same time, providing a consistent and homogeneous source of active Factor VIIa to treat Factor VIII and Factor IX deficient patients and individuals with Von Willebrand's disease, as well as providing a source of purified Factor IX for use in replacement therapy.

DISCLOSURE OF THE INVENTION

Briefly stated, the present invention discloses a DNA construct containing a nucleotide sequence which codes at least partially for Factor VII. The nucleotide sequence comprises a first nucleotide sequence encoding a calcium binding domain joined to a second nucleotide sequence positioned downstream of the first sequence. The second nucleotide sequence encodes a catalytic domain for the serine protease activity of Factor VIIa. The joined sequences code for a protein which upon activation has substantially the same biological activity for blood coagulation as Factor VIIa. The first nucleotide sequence may be substantially that of a gene encoding Factor VII, Factor IX, Factor X, Protein C, prothrombin, or Protein S. Further, the first nucleotide sequence may also encode a leader peptide corresponding to the respective gene.

In particular, the first nucleotide sequence may be derived from a genomic clone or cDNA clone of Factor VII, and may encode the leader peptide and amino-terminal portion of Factor VII. The first nucleotide sequence may also include a double-stranded oligonucleotide. A particularly preferred first nucleotide sequence is that encoding the leader peptide and amino-terminal portion of Factor IX.

In addition, the present invention discloses recombinant plasmids capable of integration in mammalian host cell DNA. One of the plasmids includes a promoter followed downstream by a set of RNA splice sites, the RNA splice sites being followed downstream by a nucleotide sequence which codes at least partially for Factor VII. The nucleotide sequence comprises a first nucleotide sequence which encodes a calcium binding domain joined to a second nucleotide sequence positioned downstream of the first sequence. The second nucleotide sequence encodes a catalytic domain for the serine protease activity of Factor VIIa. The joined sequences code for a protein which upon activation has substantially the same biological activity for blood coagulation as Factor VIIa. The nucleotide sequence is then followed downstream by a polyadenylation signal.

Similar to the recombinant plasmid noted above, the present invention also discloses a second plasmid which includes a promoter followed downstream by a set of RNA splice sites, the RNA splice sites being followed down-stream by a nucleotide sequence which codes at least partially for Factor IX. The nucleotide sequence comprises a first nucleotide sequence which encodes a calcium binding domain joined to a second nucleotide sequence positioned downstream of the first sequence. The second nucleotide sequence encodes a catalytic domain for the serine protease activity of Factor IX. The joined sequences code for a protein having substantially the same biological activity for blood coagulation as Factor IX. The nucleotide sequence is then followed downstream by a polyadenylation signal.

A third aspect of the invention discloses mammalian cells stably transfected to produce a protein having substantially the same biological activity, upon activation, as Factor VIIa. The cells are transfected with a DNA construct containing a nucleotide sequence which at least partially codes for Factor VII. The nucleotide sequence comprises a first nucleotide sequence which encodes a calcium binding domain joined to a second nucleotide sequence positioned downstream of the first sequence. The second nucleotide sequence encodes a catalytic domain for the serine protease activity of Factor VIIa. The joined sequences code for a protein which, upon activation, has substantially the same biological activity for blood coagulation as Factor VIIa.

An additional aspect of the invention discloses mammalian cells stably transfected to produce a protein having substantially the same biological activity as Factor IX. The cells are transfected with a DNA construct containing a nucleotide sequence which codes at least partially for Factor IX. The nucleotide sequence comprises a first nucleotide sequence which encodes a calcium binding domain joined to a second nucleotide sequence positioned down-stream of the first sequence. The second nucleotide sequence encodes a catalytic domain for the serine protease activity of Factor IX. The joined sequences code for a protein having substantially the same biological activity for blood coagulation as Factor IX.

The present invention further provides for a method of producing a protein having biological activity for blood coagulation mediated by Factor VIIa through establishing a mammalian host cell which contains a DNA construct containing a nucleotide sequence which codes at least partially for Factor VII. The nucleotide sequence comprises a first nucleotide sequence which encodes a calcium binding domain joined to a second nucleotide sequence positioned downstream of the first sequence. The second sequence encodes a catalytic domain for the serine protease activity of Factor VIIa. The joined sequences code for a protein which, upon activation, has substantially the same biological activity for blood coagulation as Factor VIIa. Subsequently, the mammalian host is grown in an appropriate medium and the protein product encoded by the DNA construct and produced by the mammalian host cell is isolated. The protein product is then activated to generate Factor VIIa.

Still a further aspect of the present invention discloses a method of producing a protein having biological activity for blood coagulation mediated by Factor IX. The method comprises establishing a mammalian host cell which contains a DNA construct containing a nucleotide sequence which codes at least partially for Factor IX. The nucleotide sequence comprises a first nucleotide sequence which encodes a calcium binding domain joined to a second nucleotide sequence positioned downstream of the first sequence. The second nucleotide sequence encodes a catalytic domain for the serine protease activity of Factor IX. The joined sequences code for a protein having substantially the same biological activity for blood coagulation as Factor IX. The mammalian host cell is subsequently grown in an appropriate medium and the protein product encoded by the mammalian host cell is isolated. Protein products produced by the methods noted above are also disclosed.

Other aspects of the invention will become evident upon reference to the following detailed description and attached drawings.

BRIEF DESCRIPTION OF THE DRAWINGS

FIG. 1 illustrates the partial Factor VII cDNA sequence produced by joining portions of cDNA clones pUCG700 and pUCG12.

FIG. 2a illustrates the amino acid sequences of the amino terminal regions of several clotting factors.

FIG. 2b illustrates a comparison of the amino acid sequence of Factor VII obtained from protein sequencing with that encoded by the cDNA.

FIG. 7 illustrates the nucleotide sequence of a Factor IX/Factor VII cDNA fusion.

BEST MODE FOR CARRYING OUT THE INVENTION

Figure 3:
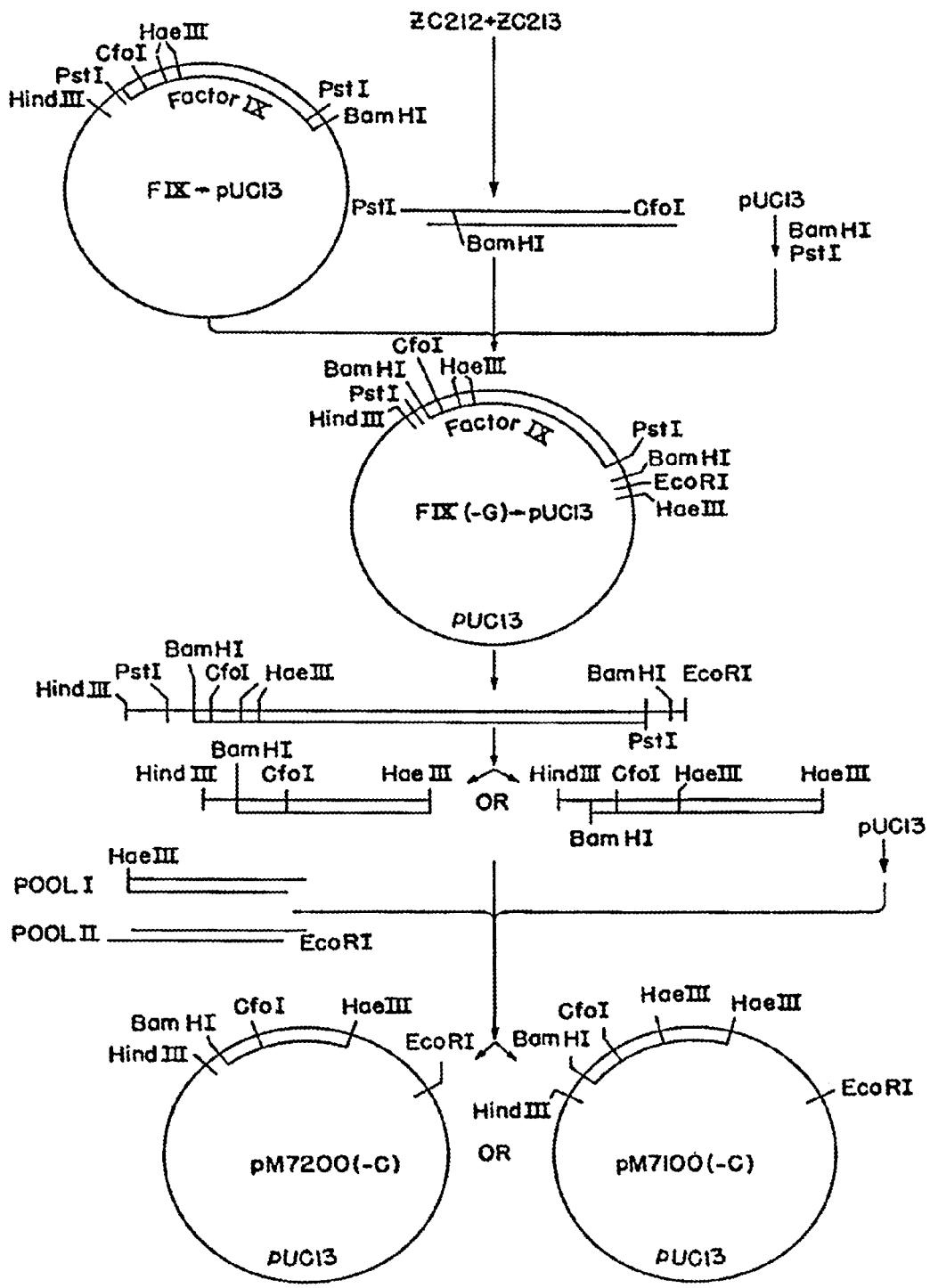
FIG. 3 illustrates the joining of Factor IX leader sequences to a sequence encoding a consensus calcium binding domain.

Prior to setting forth the invention, it may be helpful to an understanding thereof to set forth definitions of certain terms to be used hereinafter.

Complementary DNA or cDNA:

A DNA molecule or sequence which has been enzymatically synthesized from the sequences present in a mRNA template.

DNA Construct:

A DNA molecule, or a clone of such a molecule, either single- or double-stranded, which may be isolated in partial form from a naturally occurring gene or which has been modified to contain segments of DNA which are combined and juxtaposed in a manner which would not otherwise exist in nature.

Plasmid or Vector:

A DNA construct containing genetic information which may provide for its replication when inserted into a host cell. A plasmid generally contains at least one gene sequence to be expressed in the host cell, as well as sequences encoding functions which facilitate such gene expression, including promoters and transcription initiation sites. It may be a linear or closed circular molecule.

Joined:

DNA sequences are said to be joined when the 5' and 3' ends of one sequence are attached, by phosphodiester bonds, to the 3' and 5' ends, respectively, of an adjacent sequence. Joining may be achieved by such methods as ligation of blunt or cohesive termini, by synthesis of joined sequences through cDNA cloning, or by removal of intervening sequences through a process of directed mutagenesis.

Leader Peptide:

An amino acid sequence which occurs at the amino terminus of some proteins and is generally cleaved from the protein during translation. Leader peptides comprise sequences directing the protein into the secretion pathway of the cell. As used herein, the term "leader peptide" may also mean a portion of the naturally occurring leader peptide.

Domain:

A three-dimensional, self-assembling array of specific amino acids in a protein molecule which contains all or part of the structural elements necessary for some biological activity of that protein.

Biological Activity:

A function or set of functions performed by a molecule in a biological context (i.e., in an organism or an in vitro facsimile). Biological activities of proteins may be divided into catalytic and effector activities. Catalytic activities of clotting factors generally involve the activation of other factors through the specific cleavage of precursors. Effector activities include specific binding of the biologically active molecule to calcium or other small molecules, to macromolecules such as proteins, or to cells. Effector activity frequently augments, or is essential to, catalytic activity under physiological conditions. Catalytic and effector activities may, in some cases, reside within the same domain of a protein.

For Factor VIIa, biological activity is characterized by the mediation of blood coagulation through the extrinsic pathway. Factor VIIa activates Factor X to Factor Xa, which in turn converts prothrombin to thrombin, thereby initiating the formation of a fibrin clot. Because the activation of Factor X is common to both the extrinsic and intrinsic pathways of blood coagulation, Factor VIIa may be used to treat individuals severely deficient in the activities of Factor IX, Factor VIII or Von Willebrand Factor.

The biological activity of Factor IX is characterized by the mediation of blood coagulation through the intrinsic pathway. Factor IX is activated to Factor IXa by Factor XIa. Factor IXa then activates Factor X to Factor Xa in the presence of Factor VIIIa, phospholipid, and calcium ions. Factor Xa then acts in the conversion of prothrombin to thrombin, initiating the formation of a fibrin clot.

As noted above, the isolation of Factor VII from human plasma is a time-consuming and expensive process since the factor is a rare protein present only at a concentration of approximately 300 micrograms per liter of blood. In addition, it is difficult to separate from prothrombin, Factor IX and Factor X and is susceptible to proteolytic attack during purification (Kisiel and McMullen, ibid). Although single-chain human Factor VII has been purified to homogeneity (Kisiel and McMullen, ibid), the published purification methods are generally limited by low yield and/or contamination by other coagulation factors.

Factors VII and IX are produced in the liver and require vitamin K for their biosynthesis. Vitamin K is necessary for the formation of specific gamma-carboxyglutamic acid residues in the factors. These unusual amino acid residues, which are formed by a post-translational modification, bind to calcium ions and are responsible for the interaction of the protein with phospholipid vesicles. In addition, Factors VII and IX each contain one B-hydroxyaspartic acid residue which is also formed after the proteins have been translated. However, the role of this amino acid residue is not known.

Given the fact that the activities of Factors VII and IX are dependent upon post-translational modifications involving the gamma carboxylation of specific glutamic acid residues, and may also be dependent upon the hydroxylation of a specific aspartic acid residue, it is unlikely that an active product could be produced through the cloning and expression of Factors VII and IX in a microorganism.

Accordingly, the present invention provides a method of producing a protein having biological activity for blood coagulation mediated by Factor VIIa using stably transfected mammalian cells. In addition, the present invention also provides a method of producing a protein having biological activity for blood coagulation mediated by Factor IX.

As noted above, Factors VII and IX require vitamin K for their biosynthesis. In addition, the plasma proteins prothrombin, Factor X, Protein C, and Protein S also require vitamin K for their biosynthesis. The amino-terminal portions of these proteins, which contain gamma-carboxyglutamic acid residues, are homologous in both amino acid sequence and in biological function (FIG. 2a). Further, the carboxy-terminal portions of Factor VII, prothrombin, Factor IX, Factor X, and Protein C determine their specific serine protease functions.

Factor VII is a trace plasma protein, and the mRNA encoding Factor VII is believed to be rare. Consequently, purification of Factor VII from plasma in sufficient quantities to permit extensive sequence analysis and characterization remains difficult. Degradation of Factor VII during purification, even in the presence of protease inhibitors, was noted by Kisiel and McMullen (ibid). Due to these difficulties, Factor VII has been poorly characterized, compared to other more abundant components of the blood coagulation system. Indeed, the work of Kisiel and McMullen (ibid) yielded sequence information for only 10 residues of each chain of Factor VII, and in each sequence the identification of two residues was tentative. Partial amino acid sequence data for Bovine Factor VII have also been published (DiScipio et al., ibid).

The presumed rarity of Factor VII mRNA has contributed to the lack of knowledge of the Factor VII gene. The success of conventional cDNA cloning techniques is dependent on a sufficient quantity of mRNA for use as a template. Premature termination of reverse transcription results in the production of cDNA clones lacking the 5' end and this condition is exacerbated by low mRNA levels. Several strategies for cDNA cloning of low abundance message have been developed (Maniatis et al., *Molecular Cloning: A Laboratory*

*Manual*, Cold Spring Harbor Laboratory, 1982), but a lack of knowledge of the amino acid sequence of the product of interest makes it impossible to predict the DNA sequence and to design appropriate oligonucleotide probes. While it may be relatively straightforward to obtain a partial cDNA clone of a gene encoding a rare protein by using these advanced strategies, full length cDNA clones of genes encoding rare proteins such as Factor VII remain exceedingly difficult to obtain.

In comparison to Factor VII, Factor IX is a relatively abundant protein and the sequence of a cDNA clone of the human Factor IX gene is known (Kurachi and Davie, *Proc. Natl. Acad. Sci. USA* 79: 6461-6464, 1982; and Anson et al., *EMBO J.* 3: 1053-1060, 1984). The structure of the Factor IX gene has been characterized and the amino acid sequence of the protein has been determined on the basis of the known nucleotide sequence. Some protein sequence data have also been published for human and bovine Factor IX and the sequences analyzed (DiScipio et al., ibid). The amino terminal portion of the protein contains 12 glutamic acid residues that are converted to γ-carboxyglutamic acid (Gla) residues in the mature protein. The cleavage sites involved in the activation of Factor IX have also been identified (Kurachi and Davie, ibid). A sequence at the 5' end of the Factor IX cDNA clone codes for a signal peptide which is typical of those found in most secreted proteins (Kurachi and Davie, ibid). The expression of the Factor IX gene through recombinant DNA methods has not been previously reported.

Because of the difficulty in obtaining a full length cDNA clone of the Factor VII gene, three novel approaches were adopted to supply the 5' end of the coding sequence, including the region encoding the leader peptide. According to the first method, a partial cDNA clone for Factor VII is joined to a fragment encoding the leader peptide and 5' portion of Factor IX. This approach is based on the observation that the amino-terminal portions of the two molecules are responsible for the calcium binding activities of the respective proteins and the discovery that the calcium binding activity of Factor IX can substitute for that of Factor VII. The resultant polypeptide retains the biological activity of authentic Factor VII because the specific serine protease activities of the coagulation factors reside in the carboxy-terminal regions of the molecules. The second approach combines the partial cDNA clone with a DNA sequence encoding the leader and amino-terminal regions of Factor VII. The partial cDNA and amino acid sequences of Factor VII disclosed herein enable the screening of a genomic DNA library or cDNA library for clones comprising the 5' portion of the Factor VII gene. The third approach involves joining the partial cDNA clone to hybrid coding sequences comprising a cDNA fragment encoding the leader peptide of Factor IX and a synthetic gene segment encoding a consensus calcium binding domain or a predicted amino terminal sequence for Factor VII. The coding sequence for the amino terminus of Factor VII was established through previously unpublished amino acid sequence data disclosed herein. The consensus sequence was derived from the Factor VII data and published sequence data for other vitamin K-dependent plasma proteins.

The joined DNA sequences described above are then inserted into a suitable expression vector which is in turn used to transfect a mammalian cell line. Expression vectors for use in carrying out the present invention will comprise a promoter capable of directing the transcription of a foreign gene in a transfected mammalian cell. Viral promoters are preferred due to their efficiency in directing transcription. A particularly preferred such promoter is the major late promoter from adenovirus 2. Such expression vectors will also contain a set of RNA splice sites located downstream from the promoter and upstream from the insertion site for a gene encoding a protein having biological activity for blood coagulation. Preferred RNA splice site sequences may be obtained from adenovirus and/or immunoglobulin genes. Also contained in the expression vectors is a polyadenylation signal, located downstream of the insertion site. Viral polyadenylation signals are preferred, such as the early or late polyadenylation signals from SV40 or the polyadenylation signal from the adenovirus 5:EIb region. In a particularly preferred embodiment, the expression vector also comprises a viral leader sequence, such as the adenovirus 2 tripartite leader, located between the promoter and the RNA splice sites. Preferred vectors may also include enhancer sequences, such as the SV 40 enhancer.

Cloned gene sequences may then be introduced into cultured mammalian cells by calcium phosphate mediated transfection. (Wigler et al., *Cell* 14: 725, 1978; Corsaro and Pearson, *Somatic Cell Genetics* 7: 603, 1981; Graham and Van der Eb, *Virology* 52: 456, 1973.) A precipitate is formed of the DNA and calcium phosphate and this precipitate is applied to the cells. A portion of the cells take up the DNA and maintain it inside the cell for several days. A small fraction of the cells (typically $10^{-4}$) stably integrate the DNA into the genome. In order to identify these stable integrants, a gene that confers a selectable phenotype (a selectable marker) is generally introduced along with the gene of interest. Preferred selectable markers include genes that confer resistance to drugs, such as G-418 and methotrexate. Selectable markers may be introduced into the cell on a separate plasmid at the same time as the gene of interest or they may be introduced on the same plasmid. A preferred selectable marker is the gene for resistance to the drug G-418, which is carried on the plasmid pKO-neo (Southern and Berg, *J. Mol. Appl. Genet.* 1: 327-341, 1982). It may also be advantageous to add additional DNA, known as "carrier DNA," to the mixture which is introduced into the cells. After the cells have taken up the DNA, they are allowed to grow for a period of time, typically 1-2 days, to begin expressing the gene of interest. Drug selection is then applied to select for the growth of cells which are expressing the selectable marker in a stable fashion. Clones of such cells may be screened for expression of the protein of interest.

Factor VII and Factor IX produced by the transfected cells may be removed from the cell culture media by adsorption to barium citrate. Spent medium is mixed with sodium citrate and barium chloride and the precipitate collected. The precipitated material may then be assayed for the presence of the appropriate clotting factor. Further purification may be achieved through immunoadsorption. It is preferred that the immunoadsorption column comprise a high-specificity monoclonal antibody. Alternatively, purification of the barium citrate precipitated material may be accomplished by more conventional biochemical methods or by high-performance liquid chromatography.

Conversion of single-chain Factor VII to active two-chain Factor VIIa may be achieved using Factor XIIa as described by Hedner and Kisiel (*J. Clin. Invest.* 71: 1836-1841, 1983), or with other proteases having trypsin-like specificity (Kisiel and Fujikawa, *Behring Inst. Mitt.* 73: 29-42, 1983).

In summary, the present invention provides a method for the production of proteins having the activity of vitamin K-dependent blood coagulation factors using transfected mammalian cells. Gene sequences encoding the specific serine protease domains of the coagulation factors are isolated from cDNA libraries. Sequences encoding the leader peptides and calcium binding domains are isolated from cDNA or genomic libraries or constructed from synthesized oligonucleotides. The sequences are then joined in an appropriate expression vector so as to encode a protein having the desired biological activity for blood coagulation. The resulting vector and a plasmid containing a drug resistance marker are co-transfected into appropriate mammalian tissue culture cells. Transfected cells may then be selected by addition of the appropriate drug, such as G-418. The protein products are then purified from the cell growth media and assayed for biological activity in a blood coagulation assay and for immunological cross-reactivity using antibodies prepared against authentic human clotting factors.

To summarize the examples which follow, Example 1 discloses the cloning of partial cDNA sequences for Factor VII. These sequences are inserted into the bacterial plasmid pUC13 to produce plasmids pUCG700 and pUCG12. Example 2 discloses a partial amino acid sequence of human Factor VII, including the sequence of approximately 30 amino acids at the amino terminus. Example 3 discloses the construction and screening of a human genomic DNA library and the identification of genomic clones comprising Factor VII gene sequences. Example 4 discloses the construction of two hybrid gene segments, each comprising a cDNA fragment encoding the leader peptide of Factor IX and a synthesized double-stranded fragment encoding a consensus calcium binding domain. The hybrid sequences are then joined to partial cDNA clones of Factor VII. Using in vitro mutagenesis, the consensus sequence was then altered to conform to the protein sequence data for Factor VII. Example 5 describes the construction of a gene sequence encoding a fusion protein comprising the calcium binding domain of Factor IX and the specific serine protease domain of Factor VII. Example 6 describes the construction of the vector pD2 for use in expressing proteins having biological activity for blood coagulation in transfected mammalian cells. The gene fusion described in Example 5 is expressed using this vector. Example 7 describes the use of the vector pD2 to express a gene for Factor IX in a transfected mammalian cell line. Example 8 describes the construction of the vector pM7135, which contains DNA sequences encoding a primary translation product comprising the leader sequence of Factor IX fused to mature Factor VII. This vector may be used to produce mature Factor VII in a transfected mammalian cell line.

The following examples are offered by way of illustration and not by way of limitation.

EXAMPLES

Restriction enzymes were obtained from Bethesda Research Laboratories (BRL) and New England Biolabs and were used as directed by the manufacturer, unless otherwise noted. Oligonucleotides were synthesized on an Applied Biosystems Model 380 A DNA synthesizer and purified by polyacrylamide gel electrophoresis on denaturing cells. *E. coli* cells were transformed as described by Maniatis et al. (*Molecular Cloning: A Laboratory Manual*, Cold Spring Harbor Laboratory, 1982). M13 and pUC cloning vectors and host strains were obtained from BRL. Factor VII was prepared from human plasma as described by Kisiel and McMullen (ibid).

Example 1

Cloning of a Partial Factor VII cDNA

A. Construction of a Human Liver cDNA Library.

A cDNA library was prepared from human liver mRNA by the method of Chandra et al., *Proc. Natl. Acad. Sci. U.S.A.* 80: 1845-1848, 1983. The cDNA preparation was sedimented through an alkaline sucrose gradient (Monahan et al., *Biochemistry* 15: 223-233, 1976) and fractions containing species of greater than about 1000 nucleotides were pooled. The first strand preparation was made double-stranded using reverse transcriptase (Chandra et al., 1983), treated with S1 nuclease, and the residual staggered ends filled-in using DNA Polymerase I (Klenow fragment) in the presence of all four deoxyribonucleotide triphosphates (Maniatis et al., *Molecular Cloning: A Laboratory Manual*, Cold Spring Harbor Laboratory, 1982). The blunt-ended cDNA was treated with Eco RI methylase and ligated to phosphorylated Eco RI linkers using $T_4$ DNA ligase (Maniatis et al., ibid). The ligated DNA preparation was exhaustively digested with Eco RI to remove excess linker sequences and double-stranded DNAs greater than about 1000 base pairs in length were purified by neutral sucrose gradient centrifugation (Maniatis et al., ibid). Native λgt11 DNA was ligated into concatemers, digested to completion with Eco RI, and the 5' terminal phosphates were removed by treatment with bacterial alkaline phosphatase. The pooled human liver cDNA was ligated with the phage DNA, packaged in vitro (Maniatis et al., ibid), and used to infect *E. coli* Y1088 (Young and Davis, *Science,* 222: 778-782, 1983). Approximately $14 \times 10^6$ primary phage plaques were generated in this library, composed of seven libraries of $2 \times 10^6$ plaques each. Greater than 90% of these were recombinants containing human DNA inserts, based on their lack of β-galactosidase activity and characterization of 20 random clones by Eco RI digestion followed by agarose gel electrophoresis. The cDNA library, in the form of phage particles, was purified by cesium chloride gradient centrifugation and stored in SM buffer (Maniatis et al., ibid).

B. Screening of the Human Liver cDNA Library for Factor VII Clones.

The human liver expression cDNA library described above was screened for specific antigen (Young and Davis, ibid) using an $^{125}$I-labeled monoclonal Factor VII antibody prepared by the method of Brown et al. (*J. Biol. Chem.* 225: 4980-4983, 1980) using purified Factor VII. Screening of $6 \times 10^6$ phage plaques identified one isolate, designated λCG700, which gave a positive response with the antibody.

The phage clone λCG700 was tested against two other anti-Factor VII monoclonal antibodies and a rabbit polyclonal antibody to Factor VII. Isolate λCG700 gave a positive response to all these anti-Factor VII antibodies.

DNA was prepared from a plate lysate (Maniatis et al., pp. 65-66, 1982) of λCG700. Digestion of this DNA with Eco RI liberated an insert of 2139 base pairs. This insert was subcloned into M13 phage vectors (Messing, *Meth. in Enzymology* 101: 20-77, 1983; and Norrander et al., *Gene* 26: 101-106, 1983) for chain termination dideoxy DNA sequencing (Sanger et al., *Proc. Natl. Acad. Sci. U.S.A.* 74: 5463-5476, 1977). This cDNA insert contains Pst I sites at positions 214, 839, and 1205 (designated Pst Ia, Pst Ib, and Pst Ic, respectively, in FIG. 1) and a Sma I site located at position 611. The following M13 templates were sequenced:
1) full length (2139 bases) Eco RIa→Eco RIb fragment in M13mp18 (designated clone F7-1);
2) Pst Ia→Eco RIa 214 base fragment in M13mp19 (F7-2);
3) Pst Ia→Pst Ib 625 base fragment in M13mp18 (F7-3);
4) Pst Ib→Pst Ia 625 base fragment in M13mp18 (F7-7);
5) Sma I→Pst Ib 228 base fragment in M13mp10 (F7-8);
6) Pst Ib→Pst Ic 366 base fragment in M13mp18 (F7-9);
7) Pst Ic→Pst Ib 366 base fragment in M13mp18 (F7-10);
8) Pst Ic→Eco RIb 930 base fragment in M13mp19 (F7-11); and
9) Eco RIb→Eco RIa full length fragment in M13mp18 (F7-12)

(restriction site designations refer to FIG. 1).

The data confirmed the sequence on both strands for 91% of the coding region and 15% of the 3' non-coding region and yielded single-stranded sequence information for the remaining 9% of the coding region and 85% of the non-coding region.

Comparison of the amino acid sequence predicted from the cDNA sequence with the known amino acid sequence data of Kisiel and McMullen (*Thrombosis Research* 22: 375, 1981) and the amino acid sequence shown below (Example 2) revealed an anomaly which could be explained by the absence of three nucleotides in the DNA sequence near position 400. To obtain additional sequence data, λCG700 was digested with Eco RI, and the Factor VII coding fragment was inserted into pUC 13 (Vieira and Messing, *Gene* 19: 259-268, 1982; and Messing, ibid) which had been digested with Eco RI. The resultant recombinant plasmid, designated pUCG700, was digested with Xba I which cut at position 328. The digested sample was divided in half: half was labeled with $\alpha^{32}P$ dCTP and DNA Polymerase I (Klenow fragment) (Englund, P. T., *J. Mol. Bio.* 66: 209, 1972); the other half was labeled with $\gamma^{32}P$ ATP and polynucleotide kinase (Chaconas et al., *Biochem. Biophys. Res. Comm.* 66: 962, 1975). The labeled plasmids were then recut with Pst I to yield 113 and 509 base pair fragments. Both strands of each of these were sequenced by the method of Maxam and Gilbert (*Meth. in Enzymology* 74: 560, 1980). The 113 base pair fragment was sequenced in its entirety and 210 base pairs of the 509 base pair fragment were sequenced. These sequences revealed three additional bases (one C and two G's) which rendered the DNA sequence data in agreement with the protein sequence data, indicating that the previous anomalous results arose from compressions on the sequencing gel due to secondary structure involving G's and C's. The sequence of the last 9% of the coding region on both strands was also confirmed.

Further analysis of the sequence of the pUCG700 insert confirmed that a portion of this cloned fragment encoded a sequence of 11 amino acids known to be at the cleavage site of Factor VII (Kisiel and McMullen, *Thrombosis Research* 22: 375, 1981). Comparison of this sequence to Factor IX (Davie et al., ibid) and Factor X (Leytus et al., *Proc. Natl. Acad. Sci. U.S.A.* 81: 3699-3702, 1984) amino acid sequences suggested that the clone contained the sequence for Factor VII beginning at (approximately) nucleotides coding for amino acid 36 of the mature Factor VII protein and continuing through approximately 1000 coding and 1100 noncoding nucleotides and poly A sequence. In addition, it was found that this clone had frameshift mutations in the 3' coding portion.

In order to obtain the correct 3' coding region, all 14 million clones of the seven λgt11 cDNA libraries were screened by plaque hybridization (Benton and David, *Science* 196: 180-181, 1977) with nick translated cDNA of λCG700 (Maniatis et al., pp. 109-112, 1982).

Seven positive isolates were then screened by dideoxy sequencing of pUC plasmids into which the cDNA inserts had been subcloned (Wallace et al., *Gene* 16: 21, 1981). The λgt11 clones were digested with Eco RI and the Factor VII fragments were inserted into pUC13 which had been cleaved with Eco RI. All except one of these were found to start at a position corresponding to base 212 of the insert in λCG700; the one exception consisted only of 3' non-coding sequence. One of the clones starting at base 212 was selected for analysis and was designated clone pUCG12.

Because analysis of pUCG700 indicated the presence of frameshift mutations between positions 657 and 815, pUCG12 was first analyzed in this region by Maxam-Gilbert sequencing. Plasmid pUCG12 was digested with Nar I (position 779 in FIG. 1). The cut DNA was labeled with $\alpha^{32}P$ dCTP using DNA Polymerase I (Klenow fragment) and subsequently digested with Ava I (which cleaves at the same site as Sma I in FIG. 1) and Taq I (site at 1059), yielding a Nar I-Ava I 1166 bp fragment and a 200 bp Nar I-Taq I fragment. Each of these was sequenced. A C, missing in pUGC700, was found at position 697 and another C, also missing in pUCG700, was found at position 798.

The rest of the sequence of the coding region of pUCG12 was shown to be correct by sequencing by the dideoxy method on an M13 subclone of the entire insert of pUCG12. The Lac primer ZC87 (Table 1) was used to sequence from position 212 (FIG. 1) to 512; primer ZC218 (CTCTGCCT-GCCGAAC) was used to sequence from 715 to 1140 and primer ZC217 (ATGAGAAGCGCACGAAG) was used for sequencing from 720 to 350. Since the pUCG700 insert is correct from position 13 (positions 1-12 include an artificial linker) to 695, and pUGC12 is correct from position 212 to the end, the two were spliced together to yield a molecule correct from position 13 (FIG. 1) to the end. A convenient point utilized for this splice is the Xba I site at position 328. The sequence of the spliced corrected molecule is shown in FIG. 1.

Because a full-length Factor VII clone was not obtained by cDNA cloning, three strategies were adopted to provide the missing coding sequence and the necessary upstream processing and signal sequences. The first strategy was to obtain the needed sequence from a human genomic DNA library. The second approach was to synthesize the necessary 5' coding sequence, based on the amino acid sequence data for Factor VII (Example 2) and the published sequences of the genes encoding vitamin K-dependent clotting factors (Kurachi and Davie, ibid; and Davie et al., ibid), and join this to a portion of the prepro sequence of Factor IX. The third strategy relies on the functional homology of the amino terminal regions of Factor VII and Factor IX. A sequence was constructed which comprised the coding regions for the leader and amino-terminal portion of Factor IX. This was then fused in the proper orientation to the partial Factor VII cDNA.

Example 2

Amino Acid Sequence of Human Factor VII

The elucidation of the amino acid sequence of human Factor VII was desired in order to confirm the identity of putative cDNA clones, substantiate the sequence of Factor VII cDNA and provide information allowing for the synthesis of specific oligonucleotide probes to screen cDNA and genomic libraries for clones containing the 5' sequence missing from cDNA clone λCG700 and to construct a synthetic fragment encoding the amino-terminal portion of Factor VII. Although limited amino acid sequence was provided by Kisiel and McMullen (ibid), more information was sought.

Purified human Factor VIIa (Kisiel and McMullen, ibid) was reduced and carboxymethylated by the method of Crestfield et al., *J. Biol. Chem.* 238: 622, 1963. The light and heavy polypeptide chains of carboxymethylated Factor VIIa were separated by high-performance liquid chromatography (HPLC) on a Micro Pak C18 reverse phase column (Varian Corp.) by generating a gradient of 0.1% TFA in distilled water (A) and 0.1% TFA in acetonitrile (B) from 0-40% B in 5 minutes, 40-80% B in 25 minutes and 80-100% B in 5 minutes. Approximately 300 picomoles of each peptide chain were analyzed by automated Edman degradation using a Gas-Phase Protein Sequencer (Applied Biosystems, Inc.). Eighteen and 29 residues were identified at the amino-termini of the heavy and light polypeptide chains, respectively. The amino-terminal sequence of the heavy chain of Factor VIIa was consistent with that encoded by cDNA clone pUCG700 (FIG. 2b). Amino acid residues are designated within FIGS. 2a and 2b by single letter code as follows: A, alanine; C, cysteine; D, aspartic acid; E, glutamic acid; F, phenylalanine; G, glycine; H, histidine; I, isoleucine; K, lysine; L, leucine; M, methionine; N, asparagine; P, proline; Q, glutamine; R, arginine; S, serine; T, threonine; V, valine; W, tryptophan; Y, tyrosine; X indicates an unknown residue and * indicates that the Gla residues (γ) were assigned by homology to the structures of other known clotting factors and by the absence of any other phenylthiohydantoin-amino acid at those positions. The gaps (–) are placed to provide the best alignment among the sequences. In addition, the information indicated that the amino acids at positions five and nine were lysines and not threonine and arginine, respectively, as previously reported (Kisiel and McMullen, ibid). The sequence analyses of the light chain of Factor VIIa, which originates from the amino-terminal region of Factor VII, fell short by approximately 6 residues to overlap with the structure encoded by the 5' end of cDNA clone pUCG700.

To obtain additional sequence data, two nanomoles of the carboxymethylated light chain were digested for 12 hours by bovine chymotrypsin (1:100 w/w, enzyme: substrate) in 0.1 M ammonium bicarbonate, pH 7.8, at 37° C. The generated fragments were purified by HPLC on a Micro Pak C18 reverse phase column using the above solvents in a gradient of 0-30% B in 5 minutes, 30-60% B in 25 minutes and 60-80% B in 10 minutes. Peptides were identified by their U.V. absorption at 220 and 280 nm. Lyophilized peptides (approximately 1 nanomole each) were analyzed by Edman degradation. The results (FIG. 2b) confirmed much of the cDNA sequence in the corresponding region of clone pUCG700. In total, 113 of 152 residues (75%) of the light peptide chain of Factor VIIa were identified. This sequence is identical to that encoded by the known cDNA structure. Indirect evidence indicates Asn 145 is a site of carbohydrate attachment.

Example 3

Cloning of the Genomic Factor VII Sequence

As one approach to providing the 5' end sequence lacking from the cDNA, a lambda phage library containing human fetal liver DNA (Lawn et al., Cell 15: 1157-1174) was screened with nick translated Factor VII cDNA. A portion of the genomic library was plated on E. coli LE392 (ATCC 33572) to produce a total of 7.2×10⁶ plaques (Maniatis et al., ibid, pp. 320-321). The phage plaques were adsorbed from the plates onto nitrocellulose and hybridized with the ³²P-labeled cDNA according to the procedure of Benton and Davis (Science 196: 180, 1977). Eight clones were obtained and plaque purified.

Using a DNA fragment (Eco RIa-Xba I, FIG. 1) from the 5' end of the Factor VII cDNA (CG700) and standard techniques (Maniatis et al., ibid) those genomic clones containing 5' end sequences were identified. These phage were designated 7m1, 7m2 and 7m3. DNA was prepared from these recombinant phage and preliminary restriction endonuclease maps derived. Phage 7m1, which gave the strongest hybridization signal, was used to generate a more extensive restriction map and to place the Eco RI-Xba I cDNA sequences on this map by Southern blotting (Southern, J. Mol. Biol. 98: 503, 1975).

In order to determine if phage 7m1 contained the DNA sequences encoding the amino terminal amino acids of the Factor VII protein, Southern blots of phage DNA restriction digests were hybridized with mixtures of oligonucleotides whose sequences were deduced from the Factor VII amino terminal amino acid sequence. Oligonucleotides ZC188, ZC360, and ZC401 (Table 1) were radioactively labeled with T₄ polynucleotide kinase and hybridized to the phage DNA blots at a few degrees centigrade below their Tm (Wallace, R. B., et al., Nuc. Acids Res. 6: 3543-3557, 1979). The results of this analysis indicated that a 3.7 kb Sst I fragment of 7 ml contained sequences hybridizing to these oligonucleotides. This Sst I fragment was subcloned into M13 for DNA sequence analysis. Results obtained using ZC360 as sequencing primer identified a region approximately 60 nucleotides in length, which corresponded to the amino-terminal protein sequence data.

TABLE 1

| Oligo-nucleotide | Sequence |
|---|---|
| ZC87 | TCC CAG TCA CGA CGT |
| ZC188 | ```
            T    G         A
GCC GGG  CTCA  CTC CTC CA  GAA GGC GTTGG
         C    A          G
``` |
| ZC212 | GAC CTG CAG GAT CCA TGC AGC GCG TGA ACA TGA TCA TGG |
| ZC213 | GAG GCC TGG TGA TTC TGC CAT GAT CAT GTT CAC GCG CTG |
| ZC217 | ATG AGA AGC GCA CGA AG |
| ZC218 | CTC TGC CTG CCG AAC |
| ZC235 | GAT CCA TGC AGC GC |
| ZC249 | AGA ACA GCT TTG TTC TTT CA |
| ZC275 | GCC CCC ATT CTG GCA |
| ZC286 | CCA AAG AGG GCC AAC GCC TTC CTG GAG GAG AGA CCT GGG AGC CTG GAG AGA GAG TGT ATT GAG G |
| ZC287 | AAT ACA CTC TCT CTC CAG GCT CCC AGG TCT CTC CTC CAG GAA GGC GTT GGC CCT CTT TGG |
| ZC288 | AGC AGT GTA GCT TCG AGG AGA ACA GAG AGG TTT TCG AGG CCA GCG ACG |
| ZC289 | AAT TCG TCG CTG GCC TCG AAA ACC TCT CTG TTC TCC TCG AAG CTA CAC TGC TCC |
| ZC333 | CAG CTT CGT CCT GTC GCT GGC CTC |
| ZC336 | CCT CTT TGG GCC TGG TGA |
| ZC360 | ```
     C   C   C   C   G
CA  TC  TC  TC  TT  CA
     T   T   T   T   A
``` |
| ZC401 | CGT AGC GTT CAG GCC CTC GAA GAT CTC GCG GGC CTC CTC GAA GCT ACA C |

Example 4

Factor IX-Factor VII Hybrid Genes Containing a Synthesized Coding Sequence

A. Construction of a Hybrid Factor IX Leader-Synthetic Factor VII 5' Coding Sequence.

The second alternative for obtaining the 5' coding sequence for Factor VII was synthesis of an appropriate double-stranded fragment, using a nucleotide sequence predicted on the basis of the amino terminal amino acid sequence of Factor VII, the amino acid sequences of other vitamin K-dependent clotting factors, and the known nucleotide sequences of other vitamin K-dependent clotting factor genes (Kurachi and Davie, ibid; Anson et al, *EMBO J.* 3: 1053-1060, 1984; and Davie et al., ibid). In order to provide the necessary secretion and processing signals for secretion of a mature Factor VII analog, this synthetic fragment (the consensus sequence) was joined to one of two leader sequences derived from a Factor IX cDNA clone. This strategy is outlined in FIG. 3.

A cDNA coding for human Factor IX was obtained from a library made with mRNA from human liver (Kurachi and Davie, ibid). The Factor IX sequence was isolated from the pBR322 vector by digestion with Pst I and was inserted into the Pst I site of pUC13. This plasmid was designated FIX-pUC13. In order to remove the G-rich region which was present at the 5' end of the Factor IX insert as a result of cDNA cloning, a synthetic oligonucleotide adaptor was substituted for the 5' end of the cloned fragment. Oligonucleotides ZC212 and ZC213 (Table 1) were synthesized and annealed to generate a 22 base pair overlap, the fragment ends filled in and cut with appropriate restriction endonucleases, and the resulting fragment was joined to the Factor IX sequence.

To construct the adaptor, 100 pmoles each of ZC212 and ZC213 were lyophilized and resuspended in 10 ul of 10× kinase/ligase buffer (600 mM Tris pH 8.0, 100 mM $MgCl_2$, 100 nM DTT) plus 86 ul $H_2O$. The annealing reaction was run at 65° C. for 10 minutes, the mixture was slowly cooled to room temperature and put on ice. To this mixture was added 4 ul of 2.5 mM dNTP mix and 1 ul (8 units) $T_4$ DNA polymerase. The reaction was allowed to proceed 45 minutes at 14° C. Ten ul of 5 M $NH_4OAc$ was then added and the DNA was extracted once with phenol/$CHCl_3$, twice with $CHCl_3$, and was precipitated with ethanol. The DNA was centrifuged and resuspended in 100 ul medium salt buffer (Maniatis et al., ibid, p. 100), digested with 9 units Pst I and 8 units Cfo I, and extracted as above.

The modified Factor IX sequence was then constructed by combining 0.16 pmoles of the synthetic Pst I-Cfo I adaptor fragment, 0.14 pmoles of a 1.4 kb Cfo I-Bam HI Factor IX fragment from FIX-pUC13, and 0.14 pmoles of a 2.7 kb Bam HI-Pst I pUC13 vector fragment in a 20 ul reaction containing 60 mM Tris-HCl pH 7.5, 10 mM $MgCl_2$, 10 mM DTT, and 0.9 units $T_4$ ligase. The reaction was incubated for 3 h at room temperature and used to transform competent *E. coli* JM83 (Messing, Recombinant DNA Technical Bulletin, NIH Publication No. 79-99, 2, No. 2, 43-48, 1979). The cells were plated with 50 ul of 2% X-gal (5 bromo-4-chloro-3 indolyl-β-D-galactoside) on L-broth containing 40 ug/ml ampicillin and incubated at 37° C. overnight. White colonies were picked onto another plate containing ampicillin and grown at 37° C. overnight. The colonies were blotted on Whatman 540 paper and the paper prepared for hybridization according to the method of Wallace et al. (*Gene* 16: 21, 1981), except the overnight incubation on chloramphenicol plates was omitted. The papers were incubated at 44° C. for 2 h in 0.9 M NaCl, 0.09M Tris-HCl pH 7.5, 6 mM EDTA, 0.5% Nonidet P-40, 150 ug/ml *E. coli* tRNA. The papers were probed with $^{32}P$-labeled ZC235 (Table 1), a 14-mer that is specific for the altered 5' end sequence. Hybridization with $1-2\times10^6$ cpm per filter was carried out at 44° C. in the prehybridization buffer overnight. The filters were then washed 3 times in 6×SSC, 0.1% SDS at 4° C. and 3 times in 2×SSC, 0.1% SDS at 44° C. and exposed to X-ray film. Two positive clones were obtained. One of these clones was designated FIX(-G)→pUC13.

In order to confirm the sequence of the altered region of the Factor IX portion of the FIX(-G)→pUC13 construct, dideoxy sequencing directly on the pUC plasmid using the BRL reverse primer was performed using the method of Wallace et al., 1981 (ibid) using a primer end labeled with polynucleotide kinase and $\gamma^{32}P$ ATP by the method of Chaconas et al. (ibid). The sequence was as predicted.

The resulting recombinant plasmid contains three Hae III cleavage sites, the first at position 39 in the Factor IX sequence (numbering is based on the published sequence of Anson et al. (ibid), beginning at the first ATG), the second at position 130, and a third in the pUC13 polylinker. The site at 130 is a single base pair upstream from the codons for the Lys-Arg processing site of the prepro Factor IX molecule. In the final Factor IX-Factor VII hybrid constructs, the Factor IX leader sequence, terminated at position 39 or 130, was joined to a synthetic double-stranded fragment comprising the predicted consensus sequence and the last 3 codons of the Factor IX leader sequence.

The synthetic consensus fragment was produced by joining oligonucleotides ZC286-ZC289 (Table 1) to form a double-stranded fragment. One hundred pmole of each oligonucleotide was lyophilized and resuspended in 20 ul of 1× kinase buffer and incubated overnight at 4° C.; then heated at 65° C. for 10 minutes. Two pools were made using the kinased oligonucleotides. Pool 1 contained ZC286+ZC287; pool 2 contained ZC288+ZC289. The pooled pairs were annealed 10 minutes at 65° C., then cooled to room temperature over a period of 2 hours and placed on ice for 30 minutes.

The modified Factor IX fragment was removed from FIX (-G)→pUC13 as a Hind III-Eco RI fragment. Approximately 20 ug of plasmid was digested with 30 units each of Hind III and Eco RI in 100 ul Hind III buffer (BRL) containing 4 ug RNase A at 37° C. overnight. The reaction was terminated by heating at 65° C. for 10 minutes, and the vector and Factor IX fragments were electrophoresed on a 1% agarose gel and purified by electro-elution. The Factor IX fragment was precipitated with ethanol, resuspended in buffer containing 400 ng/ul RNase A, and digested with 9 units of Hae III overnight at 37° C. The Hind III-Hae III 39 base pair Factor IX fragment was isolated from this digest by electrophoresis on a 1.5% agarose gel followed by electro-elution. To obtain the Hind III-Hae III 130 base pair Factor IX fragment, FIX-pUC13 was digested with Eco RI and Hind III and the Factor IX fragment isolated as above. Approximately 3 ug of this Hind III-Eco RI fragment was digested with 6 units of Hae III at 37° C. and aliquots were removed at five minute intervals over 30 minutes into a solution containing 50 mM-EDTA. The aliquots were pooled and the Hind III-Hae III 130 base pair fragment was purified by electrophoresis on a 5% acrylamide gel followed by electro-elution.

The final Factor IX-consensus sequence hybrids were prepared by joining, in a four-part ligation, oligonucleotide pools 1 and 2, Factor IX Hind III-Hae III (39 or 130 base pairs), and pUC13 Hind III-Eco RI. The resulting plasmids were used to transform *E. coli* HB101 (ATCC 33694). Colonies were screened by digestion of DNA with Eco RI and Hind III. The sequence comprising the 39 base pair Factor IX sequence joined to the synthetic consensus sequence is hereinafter referred to as mini-FIX-FVII. The plasmid containing this construct was designated pM7200(-C). The sequence comprising the 130 base pair Factor IX sequence joined to the synthetic consensus sequence is referred to as maxi-FIX-FVII. The plasmid containing this construct was designated pM7100(-C). The consensus sequence encodes a polypeptide comprising the amino acid sequence Ala-Asn-Ala-Phe-Leu-Gla-Gla-Gla-Arg-Pro-Gly-Ser-Leu-Gla-Arg-Gla-Cys-Lys-Gla-Gln-Cys-Ser-Phe-Gla-Gla-Ala-Arg-Gla-Ile-Phe-Gla-Gly-Leu-Asn-Arg-Thr-Lys-Leu.

B. Joining Factor IX-Consenus Sequence Hybrid Fragment to Factor VII cDNA Clone.

Figure 4:
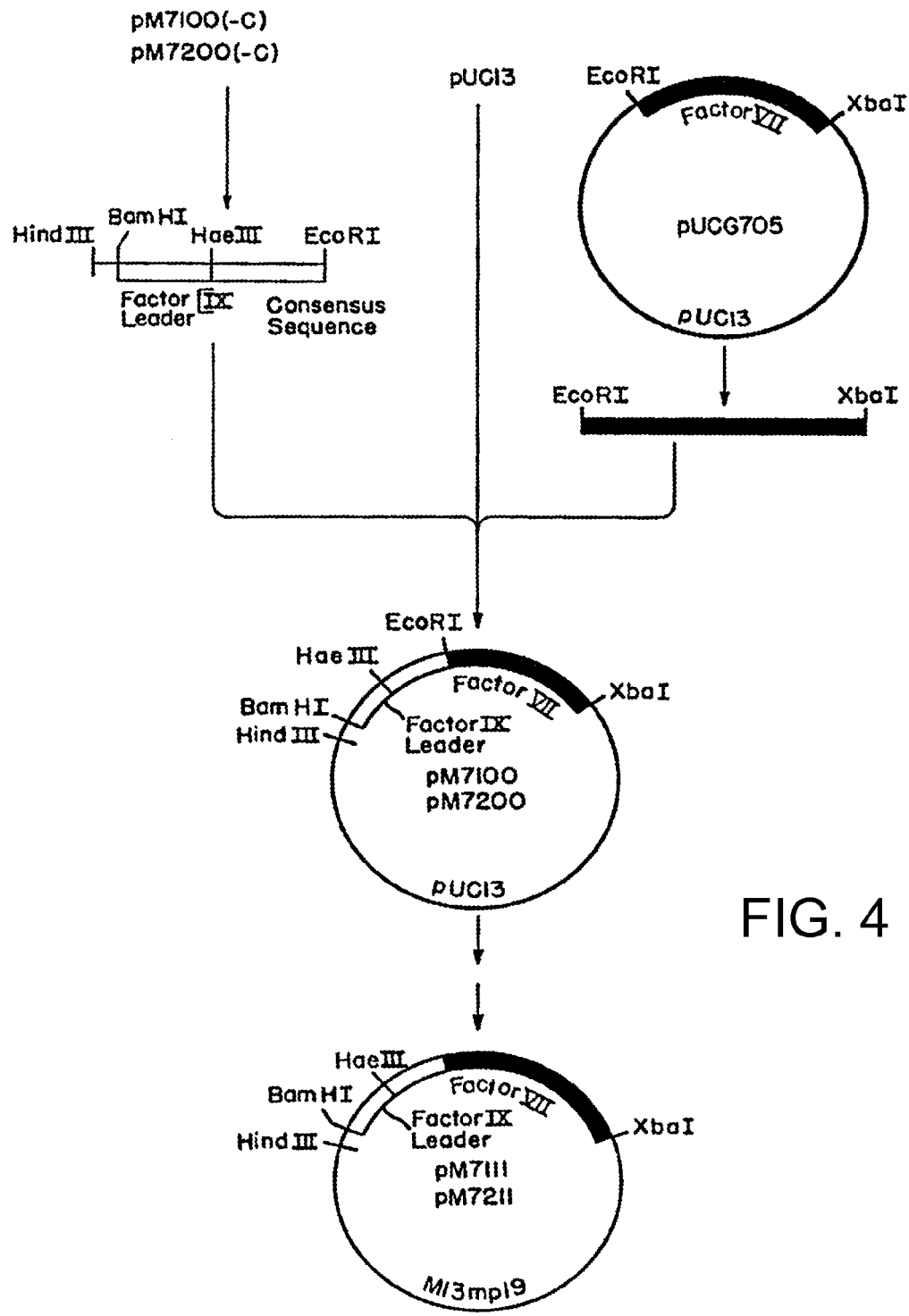
FIG. 4 illustrates the joining of the Factor IX-consensus sequence hybrids to a partial Factor VII cDNA to produce an in-frame coding sequence.
Figure 5:
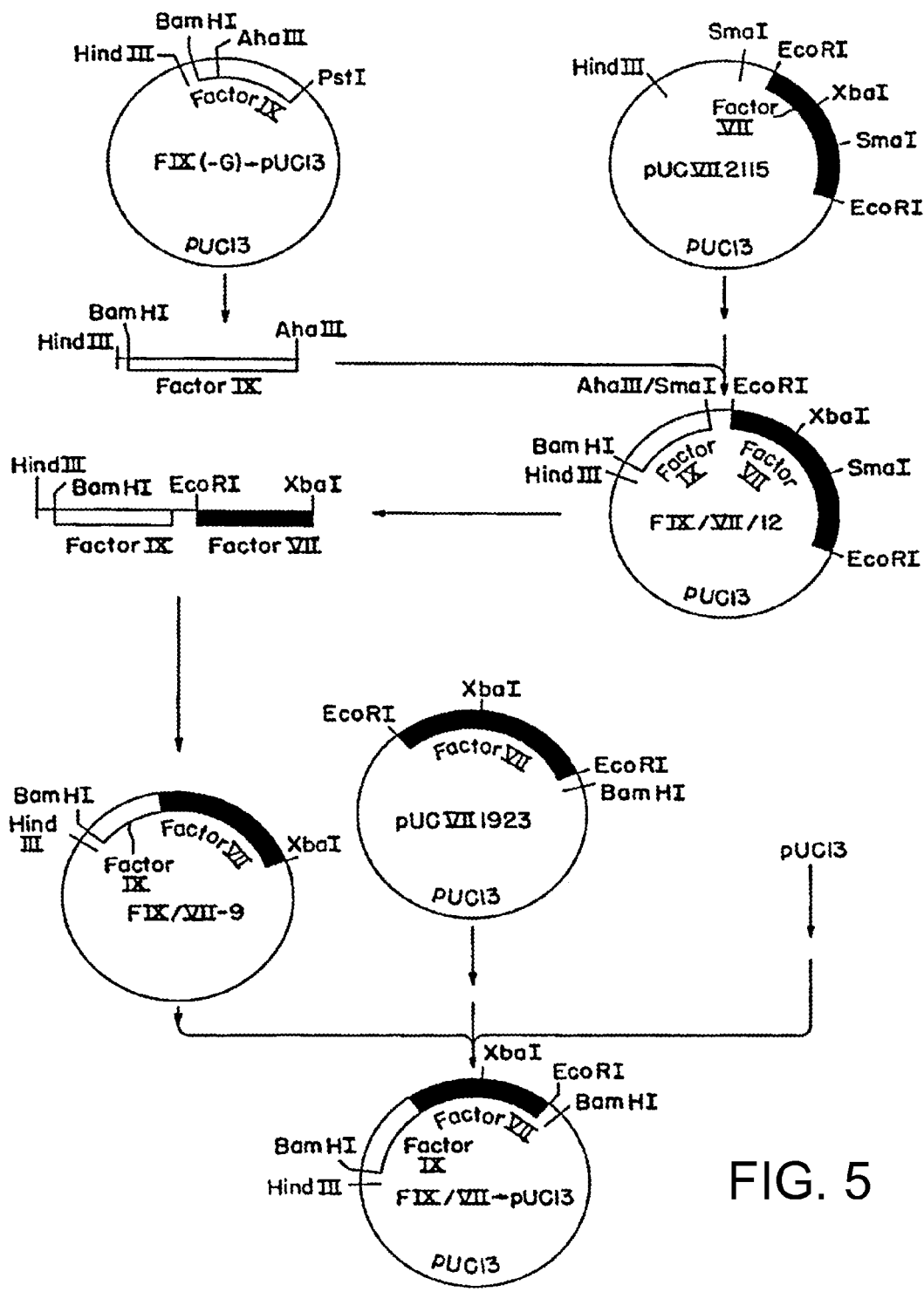
FIG. 5 illustrates the construction of a plasmid containing a coding sequence for a Factor IX/Factor VII fusion protein.

The Factor IX-consensus sequence hybrids (either mini or maxi) were joined to the 5' portion of the Factor VII cDNA and the vector pUC13 in a three-part ligation (FIGS. 4 and 5). The vector fragment was produced by digesting 6 ug of pUC13 with 10 units each of Xba I and Hind III in Hind III buffer containing RNase A (400 ng/ul). The mini-FIX-FVII fragment was produced by digesting 2 ug of pM7200(-C) with 10 units each of Hind III and Eco RI as above. The maxi-FIX-FVII fragment was similarly prepared from pM7100(-C). The 5' portion of the Factor VII cDNA was prepared from plasmid pUCG705 (comprising the Eco RI-Xba 5' fragment of pUCG700 subcloned into pUC13) by digestion with Xba I and Eco RI. Digests were run at 37° C. for 2 hours and the products were separated by electrophoresis on a 1.5% agarose gel. The desired fragments were electro-eluted, extracted with phenol/CHCl$_3$ and CHCl$_3$, and precipitated with ethanol. The three fragments, pUC13/Xba I-Hind III, Factor IX-Factor VII (mini or maxi)/Hind III-Eco RI, and 5' Factor VII/Eco RI-Xba I were then ligated in 20 ul of ligase buffer containing 2 ul 20 mM ATP and 0.9 unit T$_4$ DNA ligase overnight at 4° C. Colonies were screened by restriction analysis with Hind III and Xba I. The recombinant plasmids containing the mini- and maxi-FIX-FVII sequences were designated pM7200 and pM7100, respectively (FIG. 4).

Due to the linker addition used in producing the Factor VII cDNA, modifications had to be made in the fusion sequences to generate correct in frame coding sequences. Both mini- and maxi-fusions contain an Eco RI site at the junction between the Factor IX-consensus sequence hybrid and the Factor VII cDNA which is an artifact of the cDNA cloning process. In addition, the mini-fusion requires the addition of a C to change the sequence at the Hae III site from 5'AGGCCA3' to 5'AGGCCCA3' and establish the correct reading frame downstream of this sequence. These corrections were made by oligonucleotide-directed site specific mutagenesis, essentially as described for the two-primer method by Zoller and Smith (*Manual for Advanced Techniques in Molecular Cloning Course*, Cold Spring Harbor Laboratory, 1983). The mini-FIX-FVII fragment was removed from pM7200 by digestion with Hind III and Xba I and inserted into M13mp19. The maxi-FIX-FVII fragment was purified from pM7100 and subcloned in a similar manner. The mutagenic primers ZC333 and ZC336 (see Table 1) were used for removal of the Eco RI site and the base insertion, respectively. In each case, the universal primer ZC87 was used as the second primer. The mutagenic primers were phosphorylated by combining 40 pmoles of primer and 60 pmoles ATP with 1 unit of T$_4$ DNA kinase overnight at 60° C. To remove the Eco RI site from the maxi-FIX-FVII hybrid, 1 ug of the M13 single-stranded template was combined with 20 pmoles each ZC333 and ZC87 in a total volume of 10 ul. The primers were annealed to the template for 10 minutes at 65° C., cooled to room temperature for 5 minutes, then placed on ice for 5 minutes. The primers were extended using DNA polymerase I (Klenow fragment). To remove the Eco RI site and correct the reading frame in the mini-FIX-FVII hybrid, 1 ug of the appropriate M13 single-stranded template was combined with 20 pmoles each ZC333, ZC336 and ZC87. Annealing and primer extension reactions were carried out as described above. Plaque lifts were screened with $^{32}$P-labeled primer (ZC333 or ZC336) at 60° C. and sequences confirmed by dideoxy sequencing. The resultant constructs, comprising the maxi- and mini-FIX-FVII sequences, were designated pM7111 and pM7211, respectively.

The consensus sequence contains several regions which, do not conform to the protein sequence data obtained for Factor VII (FIG. 2). In order to produce a sequence which encodes a polypeptide with greater homology to the amino-terminal portion of Factor VII, the consensus sequence was altered by oligonucleotide-directed site-specific mutagenesis. The changes made were the insertion of Leu at position 8, substitution of Ile for Lys at position 18 (numbers refer to the amino acid position after the insertion at position 8), Asn for Ala at position 26, and the sequence Ala-Ser-Asp for Gly-Leu-Asn at positions 32-34 (based on tentative amino acid sequence data).

The sequence changes at positions 8 and 18 were made using pM7111 (sense strand) as template. Primers ZC352 (5'CCC AGG TCT CAG CTC CTC CAG3') and ZC353 (5'CTG CTC CTC CTT ACA CTC TCT3') were annealed to the template and extended as described above. The resultant phage clone was designated pM7114. The sequence of the insert in pM7114 was confirmed by dideoxy sequencing.

In a similar manner, the changes at positions 26-34 were made on the pM7114 template (sense strand) using the mutagenic primer ZC366 (5'CAG CTT CGT CCT GTT CAG GCC CTC GAA GAT CTC GCG GGC CTC CTC GAA3') and ZC87 (Table 1) as second primer. The resultant construct was designated pM7115. The sequence of the entire 550 bp insert in the M13 vector was determined by dideoxy sequencing and found to be correct.

Example 5

Construction of Factor IX-Factor VII cDNA Fusion

The Factor IX-Factor VII cDNA fusion was prepared using Factor IX cDNA obtained from a human liver cDNA library as described by Kurachi and Davie (ibid) and the Factor VII cDNA sequence described in Example 1.

The fusion point chosen for the hybrid protein was between amino acid +38 (threonine) of Factor IX and the first lysine encoded by the Factor VII cDNA sequence. Such a protein would be encoded by a sequence consisting of the first 252 bp of the Factor IX cDNA sequence and all of the cloned Factor VII cDNA sequence except the first two codons. To construct this hybrid sequence, the Factor IX sequence was first fused to pUCG700 using convenient restriction sites. This fusion resulted in the plasmid FIX/VII/12 (described below) which contains the first 310 bp of the Factor IX cDNA joined to the entire Factor VII cDNA sequence. To achieve the precise junction desired for the hybrid protein, the intervening base pairs were removed by oligonucleotide-directed mutagenesis.

Joining of the Factor IX cDNA sequence to Factor VII cDNA sequence was accomplished by ligating a 0.3 kb Hind III-Aha III fragment of FIX(-G)→pUC13 (Example 4) to a 4.7 kb Sma I-Hind III fragment from pUCG700 (FIG. 5). The Hind III-Aha III fragment was prepared by digesting 3 ug of FIX(-G)→pUC13 with 40 units of Hind III in 40 ul of medium salt buffer (Maniatis et al., ibid) at 37° C., 4 hours. The volume was then increased to 100 ul of medium salt buffer, and 5 units of Aha III were added and the 37° C. incubation continued for 18 hours. The DNA fragments were separated by electrophoresis in 1% agarose and the 0.3 kb band isolated as described above. A Sma I partial digestion of pUCG700 was obtained by incubating 3 ug of pUCG700 at 25° C. for 1 hour with 4.8 units of Sma I in a reaction volume of 30 ul. The reaction was stopped by a 15-minute incubation at 65° C. The sample was then extracted once with an equal volume of phenol and ethanol precipitated.

The precipitate was collected by a 10-minute microfuge spin, rinsed with 70% ethanol and air dried. The DNA was redissolved in 30 ul of medium salt buffer and digested with 30 units of Hind III at 37° C. for 3 hours. The DNA was subjected to electrophoresis in 0.7% agarose and the 4.7 kb Hind III II-Sma I fragment isolated as described above. Equimolar amounts of the two fragments (0.048 pmoles) were ligated in a 10 ul reaction containing 50 mM Tris-HCl pH 7.5, 10 mM MgCl$_2$, 1 mM DTT, 1 mM ATP, and 3 units of T$_4$ DNA ligase at 14° C. for 3.5 hours and then used to transform competent *E. coli* RRI (ATCC 31343). The cells were grown on ampicillin plates and 12 of the resulting colonies were screened by restriction enzyme digestion for the presence of the desired plasmid construction. DNA from colony 12 (FIX/VII/12) gave the expected restriction enzyme digestion pattern and was used in the next step of the hybrid gene construction.

The oligonucleotide-directed mutagensis procedure was performed on a single-stranded DNA template. Thus, it was necessary to clone the fused Factor IX/Factor VII sequences into M13mp19. To obtain a conveniently small DNA fragment, a 640 bp Hind III-Xba I fragment was isolated from FIX/VII/12. This fragment contains 310 bp of the 5' end of Factor IX cDNA and 330 bp of the Factor VII sequence. The vector was prepared by digesting 1 ug of M13mp19 RF DNA with 20 units of Hind III and 20 units of Xba I in 40 ul of medium salt buffer at 37° C. for 18 hours. The DNA was subjected to electrophoresis in 1.2% agarose and the linear 6.4 kb fragment isolated from the gel as described above. Five ug of FIX/VII/12 DNA was digested with 10 units of Xba I in 40 ul of medium salt buffer at 37° for 18 hours. Twenty units of Hind III were added and the digestion continued at 37° C. for an additional 7 hours. The resulting fragments were separated by electrophoresis in 1.2% agarose and the 640 bp fragment eluted as above. Ten ng of linearized M13mp19 and 1 ng of the 640 bp fragment were ligated at 14° C. for 1 hour and then used to transform competent *E. coli* JM101 (Messing, *Meth. in Enzymology*, ibid). The cells were plated with X-gal and IPTG (Messing, *Meth. in Enzymology*, ibid) and eight light blue plaques were picked and used to infect 2.5 ml cultures of *E. coli* JM103 at $A_{600}$=0.3. After 18 hours' growth at 37° C., the cells were harvested by centrifugation in a room temperature clinical centrifuge and 20 ul of the supernatant which contains the M13 phage was mixed with 10 ug/l ethidium bromide. By comparison with known standards, each of the eight clones had an insert of approximately the correct size. Single-stranded DNA was then prepared from 1.5 ml of the supernatants as described by Messing (*Meth. in Enzymology*, ibid). This construct was then sequenced with the dideoxy method using the oligonucleotide ZC87 as a primer to confirm that the insert junction was correct. One of the correct clones (#4) was used as a template in oligonucleotide-directed mutagenesis to produce a functional Factor IX-Factor VII fusion.

The oligonucleotide ZC249, a 20-mer consisting of 10 bp of the desired Factor IX sequence and 10 bp of the desired Factor VII sequence (Table 1) was used as the mutagenic primer. The oligonucleotide ZC87, which hybridizes to the M13mp19 sequence, was used as the second primer.

The mutagenesis procedure used was modified from that of Zoller and Smith (ibid). For the annealing reaction, 20 pmoles of ZC249 were phosphorylated by incubating overnight at 4° C. in 20 ul 60 mM Tris-HCl pH 8.0, 10 mM MgCl$_2$, 1 mM DTT, 1 mM ATP, 1 unit T$_4$ kinase. The reaction was stopped by incubation at 65° C. for 15 minutes, and the sample was lyophilized. One pmole of single-stranded clone #4 template and 20 pmole of ZC87 were added in 10 ul annealing buffer (200 mM Tris-HCl pH 7.5, 100 mM MgCl$_2$, 500 mM NaCl, 10 mM DTT). The sample was heated to 65° C. for 10 minutes, incubated at room temperature for 5 minutes, and then placed on ice. Ten ul of the following solution was prepared fresh and added to the sample: 20 mM Tris-HCl pH 7.5, 10 mM MgCl$_2$, 10 mM DTT, 1 mM dNTPs, 1 mM ATP, 0.15 units/ul T$_4$ DNA ligase, 0.25 units/ul *E. coli* DNA Polymerase I (Klenow fragment). The reaction was then incubated at 15° C. for 3 hours and the sample used to transform competent *E. coli* JM101 (Messing, *Meth. in Enzymology*, ibid).

The resulting plaques were lifted onto nitrocellulose and screened by hybridization to $^{32}$P-labeled ZC249. Dry BA85 filters (Schliecher & Schuell, 0.45 um) were laid onto the agar plate and the phage allowed to adsorb for 5 minutes. The filters were removed and allowed to dry for 5 minutes, placed on Whatman 3 MM paper, saturated in 0.5 M NaOH, 1.5 M NaCl for 5 minutes, air dried for 3 minutes, placed on Whatman paper, saturated in 1 M Tris-HCl pH 8, 1.5 M NaCl, for 5 minutes, and air dried for 3 minutes. The Tris-HCl step was repeated and the filters were rinsed in 100 ml 6×SSC for 2 minutes at room temperature. After air drying, the filters were baked at 80° C. for 2 hours and prehybridized at 47° C. (T$_m$−4° of ZC249) overnight in 6.7×SSC pH 6.5, 2 mg/ml *E. coli* tRNA, and 0.2% (w/v) each BSA, Ficoll, and polyvinylpyrrolidine.

After the prehybridization step, the filters were incubated with 2.5×10$^6$ cpm/filter of labeled ZC249 in the same SSC hybridization buffer at 47° C. overnight. Following hybridization, the filters were washed 3 times, 5-10 minutes each, at room temperature in 6×SSC and exposed to X-ray film. Putative positive plaques were replated and screened as above. Individual plaques were then picked, and single-stranded DNA was prepared and sequenced using ZC275 as a primer. The oligonucleotide ZC275 corresponds to a sequence 40 bp in the 5' direction of ZC249 on the same strand (Table 1).

Four positive plaques were identified. The entire insert in M13mp19 for one clone (FIX/VII-9) was sequenced by the dideoxy method using the oligonucleotides ZC87 and ZC275 and determined to be correct. The confirmed sequence is represented by bases 1-567 in FIG. 7. RF DNA from this clone was then used for the final step in the construction of the hybrid gene.

Three fragments were used to make the final construction: the 0.6 kb Hind III-Xba I fragment from FIX/VII-9 containing the fused IX/VII sequences; a 1.7 kb Xba I-Bam HI Factor VII cDNA fragment from pUCG12; and a 2.7 kb Bam HI-Hind III fragment of pUC13. Three ug of FIX/VII-9 (RF DNA) were digested at 37° C. for 6 hours with 45 units of Xba I in a volume of 50 ul. The DNA was precipitated with ethanol, resuspended and digested at 37° C. for 4 h with 50 units of Hind III. The sample was subjected to electrophoresis in 1% agarose and the 0.6 kb band electro-eluted onto NA45 paper (Schliecher & Schuell). The DNA was eluted from the paper with 1.5 M NaCl, 50 mM Tris-HCl pH 8, 1 mM EDTA, phenol extracted and precipitated with ethanol.

To obtain the remaining Factor VII cDNA sequence, 5 ug of pUCG12 was digested at 37° C. for 3 hours with 36 units of Xba I in 40 ul of medium salt buffer. Then 8 ul of 10× high salt buffer, 28 ul of H$_2$O, and 4 ul (40 units) of Bam HI were added and the reaction incubated at 37° C. for 3 hours. The DNA fragments were separated by electrophoresis in 1% agarose and the 1.7 kb fragment isolated as described above.

The vector fragment was prepared by digesting 1 ug of pUC13 with 10 units of Hind III in 20 ul of medium salt buffer at 37° C. for 1 hour. Two ul of 10× high salt buffer and 10 units of Bam HI were then added and the incubation continued for another 2 hours. The DNA was purified on a 1% agarose gel as described above.

Equimolar amounts (approximately 0.56 pmoles) of the three fragments were ligated at room temperature for 45 minutes in 10 ul of 50 mM Tris-HCl pH 7.5, 10 mM $MgCl_2$, 1 mM DTT, 1 mM ATP and 3 units $T_4$ DNA ligase. The reaction mixture was used to transform competent E. coli JM83. The cells were plated on medium containing 40 ug/ml ampicillin with 50 ul of 2% X-gal added to each plate. DNA was prepared from 7 white colonies and then screened by restriction enzyme digestion. One of the clones giving the correct pattern was designated FIX/VII→pUC13.

Example 6

Expression of Biologically Active Factor VII Analogs

The mammalian cell expression vector pD2 was chosen for expression of the FIX/VII gene in transfected animal cells. It was constructed from plasmid pDHFR-III (Berkner and Sharp, *Nuc. Acids Res.* 13: 841-857, 1985) in the following manner. The Pst I site abutting the DHFR cDNA in pDHFR III was converted to a Bam HI site by conventional linkering (Scheller, R. H., Dickerson, R. E., Boyer, H. W., Riggs, A. D., and Itakura, K., *Science* 196: 177-180, 1977). The pDHFR III DNA was incubated with 10 mM Tris pH 7.6, 6 mM β-MSH, 6 mM NaCl, 10 mM $MgCl_2$ and 2.5 units Pst I for 10 minutes at 37° C., followed by phenol extraction and ethanol precipitation. The Pst I cohesive termini were blunt ended using $T_4$ DNA polymerase. After phenol extraction and dialysis against 10 mM Tris pH 8.0, 1 mM EDTA, 0.3 M NaCl, the DNA was ethanol precipitated. The DNA was resuspended in 20 ul 1.4 mM ATP, 50 mM Tris pH 7.6, 10 mM $MgCl_2$, 1 mM dithiothreitol and then incubated with 5 ng of $T_4$ polynucleotide kinase-treated Bam HI linkers (New England Biolabs) and 200 units of $T_4$ polynucleotide ligase for 12 hours at 12° C., followed by phenol extraction and ethanol precipitation. The DNA was digested with 90 units of Bam HI at 37° C. for 1 hour, followed by electrophoresis through a 1.4% agarose gel. The 4.9 kb DNA fragment (corresponding to pDHFR III DNA lacking the DHFR cDNA and SV40 polyadenylation signal) was electro-eluted and recircularized with polynucleotide ligase and then transfected into E. coli HB101. Ampicillin-sensitive colonies were screened by rapid prep analysis (Birnboim, H. C., and Doly, J., *Nucleic Acids Research* 7: 1513-1523, 1979) and the correct clone was grown up to generate a large-scale plasmid DNA preparation.

The resultant plasmid was cleaved with 20 units Bam HI and treated with 2.5 ug calf intestinal phosphatase and electrophoresed on a 1.4% agarose gel. Twenty-five ug of pSV40 (a clone of SV40 DNA inserted into the Bam HI site of pBR322) were digested with 25 units of Bcl I for 1 hour at 50° C., followed by the addition of 25 units of Bam HI, and the incubation continued for 1 hour at 37° C. This DNA was then electrophoresed on a 1.4% agarose gel. The Bam HI-cut vector (i.e., that lacking the polyadenylation signal) was joined to the SV40 DNA fragment (0.14 to 0.19 map units [Tooze, J., ed., "DNA Tumor Viruses, Molecular Biology of Tumor Viruses"]) containing the late polyadenylation signal by incubating the gel-purified fragments (0.1 ug each) in 20 ul 50 mM Tris pH 7.6, 10 mM $MgCl_2$, 1 mM dithiothreitol, 1.4 mM ATP and 100 units $T_4$ polynucleotide ligase for 4 hours at 12° C., followed by transformation into E. coli RR1. Positive colonies were identified by rapid prep analysis, and a large-scale plasmid preparation of the correct DNA, pD2, was prepared.

Figure 6:
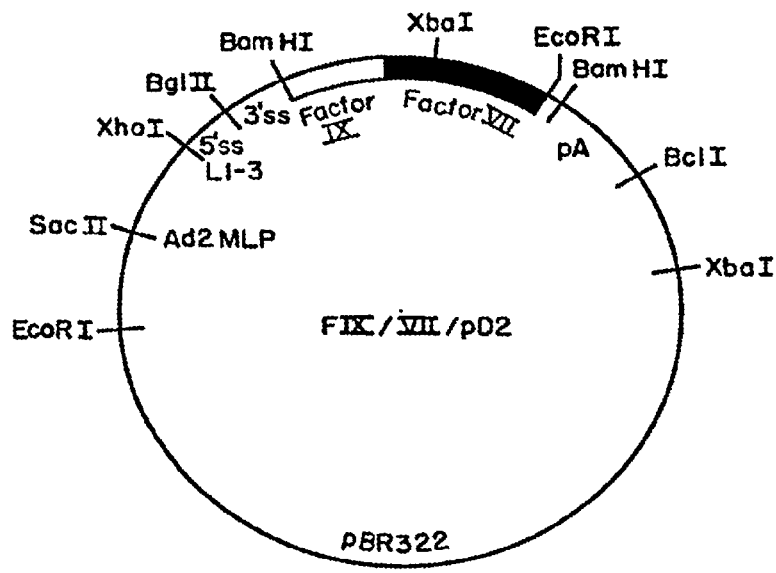
FIG. 6 illustrates the expression vector FIX/VII/pD2. Symbols used are Ad2 MLP, the major late promoter from adenovirus 2; L1-3, the adenovirus 2 tripartite leader sequence; 5'ss, 5' splice site; 3'ss, 3' splice site; and pA, the late polyadenylation signal from SV40.

To make the Factor IX/VII expression construction, 1 ug of pD2 was digested at 37° C. for 1 hour with 20 units of Bam HI in 20 ul of high salt buffer. Twenty ul of 10 mM Tris-HCl pH 8, 1 mM EDTA and 0.1 unit of calf alkaline phosphatase (Boeringer) were then added. The reaction was incubated at 37° C. for 1 hour and stopped by heating to 75° C. for 10 minutes. Ten ug of FIX/VII→pUC13 was digested at 37° C. for 2 hours with 150 units of Bam HI in 150 ul of high salt buffer. The DNA fragments were separated by electrophoresis in 1.2% agarose and the 2.3 kb fragment was isolated. Equimolar amounts (0.015 pmoles) of the 2.3 kb Bam HI fragment and the pD2 vector fragment were ligated at 14° C. for 2.5 hours as above. The reaction mixture was used to transform E. coli RR1 cells, which were then plated on medium containing 10 ug/ml ampicillin. Plasmid DNA was prepared from 12 of the resulting colonies and screened by restriction enzyme digestion. One of the clones with the correct enzyme digestion pattern was designated FIX/VII/pD2 (FIG. 6). E. coli RR1 transformed with FIX/VII/pD2 has been deposited with ATCC under accession number 53068.

The procedure used to transfect baby hamster kidney (BHK) cells (available from American Type Culture Collection, accession number CCL10) with FIX/VII/pD2 was similar to published methods (for example, Wigler et al., *Cell* 14: 725, 1978; Corsaro and Pearson, *Somatic Cell Genetics* 7: 603, 1981; Graham and Van der Eb, *Virology* 52: 456, 1973). The BHK cells were grown at 37° C., 5% $CO_2$, in Dulbecco's media (plus 10% heat-inactivated fetal calf serum and supplemented with glutamine and penicillin-streptomycin) in 60 mm tissue culture Petri dishes to a confluency of 20%. A total of 10 ug DNA was used to transfect one 60 mm dish: 3.75 ug of FIX/VII/pD2, 1.25 ug of pKO-neo (Southern and Berg, *J. Mol. Appl. Genet.* 1: 327-341, 1982) and 5 ug of salmon sperm DNA. The DNAs were precipitated in 0.3 M NaOAc, 75% ethanol, rinsed with 70% ethanol and redissolved in 20 ul 10 mM Tris-HCl pH 8, 1 mM EDTA. The DNA was combined with 440 ul $H_2O$ and 500 ul of 280 mM NaCl, 1.5 mM $NaHPO_4$, 12 mM dextrose, 50 mM HEPES pH 7.12. Sixty ul of 2 M $CaCl_2$ were added dropwise to the above mixture and the solution let stand at room temperature for 30 minutes. The solution was then added to the cells and the cells returned to 37° C. for 4 hours. The medium was removed and 5 ml of 20% DMSO in Dulbecco's with serum were added for 2 minutes at room temperature. The dish was then washed rapidly with 2 changes of medium and incubated in fresh medium overnight. Twenty-four hours after the DNA was added, the medium was removed and selective medium added (10 mg/ml of G418, 498 ug/mg, Gibco, in Dulbecco's with serum). After 10 and 13 days, individual clones, representing cells that had incorporated the pKO-neo gene and were thus resistant to G418, were transferred to 96-well (or 24-well) plates and grown up for protein assays.

Cells were grown in Dulbecco's plus 10% fetal calf serum containing 5 ug/ml vitamin K (Phytonadione, Merck). The medium was separated from the cells and cellular debris by centrifugation, and assayed for Factor VII polypeptide (by ELISA) and for biological activity. The cells were removed from the plates with trypsin, washed with fresh medium, centrifuged, and frozen at −20° C. The cell pellets were then thawed in PBS, pelleted, and resuspended in PBS containing 0.25% Triton X-100. Samples were diluted and assayed for polypeptide and activity.

The ELISA for Factor VII was done as follows. Two hundred microliters of a monoclonal antibody against human Factor VII (5 ul/ml in 0.1 M $Na_2CO_3$ pH 9.6) were incubated in each well of a 96-well microtiter plate 2 hours at 37° C. The wells were then incubated with 220 ul of 1% bovine serum albumin (BSA) and 0.05% Tween 20 in PBS pH 7.2 2 hours at 37° C. The plates were rinsed with $H_2O$, air dried, and stored at 4° C. To assay samples, 200 ul samples were incubated 1 hour at room temperature in the antibody-coated wells. The wells were then rinsed four times with 200 ul PBS containing 0.05% Tween 20. The wells were then incubated for 1 hour at room temperature with 200 ul of an IgG fraction of rabbit polyclonal antiserum against Factor VII (5 ug/ml in PBS containing 1% BSA and 0.05% Tween 20). This was followed by incubation with goat anti-rabbit IgG coupled to alkaline phosphatase. The wells were then rinsed four times with PBS containing 0.05% Tween 20. To the wells were added 200 ul p-nitrophenyl phosphate (30 mg) dissolved in diethanolamine buffer (96 ml per liter) pH 9.8 containing 56 mg/l $MgCl_2$. The enzyme reaction was done at 37° C. and the development of a yellow color was monitored at 405 nm using an ELISA plate reader. Results obtained for cell media are given in Table 2.

Factor VII biological activity was assayed by the one-stage clotting assay described by Quick (*Hemorragic Disease and Thrombosis,* 2nd ed., Leat Febiger, Philadelphia, 1966). Results obtained for cell media are given in Table 2.

TABLE 2

| Day | Cells/ml ($\times 10^{-4}$) | Factor VII polypeptide ng/ml | Factor VII activity (ng/ml) |
|---|---|---|---|
| 1 | 2.9 | 25 | 6.0 |
|   | 2.7 |   |   |
| 2 | 1.9 | 47 | 15.9 |
|   | 2.8 |   |   |
| 3 | 1.96 | 160 | 93 |
|   | 2.26 |   |   |
| 4 | 4.71 | 550 | 300 |
|   | 4.14 |   |   |
| 5 | 8.79 | 725 | 531 |
|   | 11.28 |   |   |
| 6 | 5.1 | 975 | 600 |
|   | 8.4 |   |   |

Example 7

Expression of Factor IX

Fourteen ug of FIX(-G)→pUC13 were digested with 30 units of Bam HI in 30 ul of high salt buffer for 3 hours at 37° C. The DNA was then subjected to electrophoresis in 1% agarose and the 1.4 kb band containing the Factor IX sequence was isolated from the gel.

Three ug of the vector pD2 were digested with 30 units of Bam HI in 30 ul high salt buffer for 3 hours at 37° C. The DNA was subjected to electrophoresis in 1% agarose and the linear 1.5 kb fragment isolated. The DNA was then treated with 0.12 units calf alkaline phosphatase in 30 ul of 10 mM Tris-HCl pH 8, 1 mM EDTA for 30 minutes at 37° C. The salt was adjusted to 0.3 M NaOAc and the sample extracted twice with phenol, once with chloroform and the DNA was ethanol precipitated. The pellet was rinsed in 70% ethanol, dried and redissolved in 20 ul 10 mM Tris-HCl pH 8, 1 mM EDTA. Equimolar amounts (0.02 pmoles) of the two fragments were ligated with 10 units of $T_4$ DNA ligase as described above. The reaction mixture was used to transform *E. coli* RR1 cells. DNA from twelve of the resulting ampicillin-resistant colonies was screened by restriction enzyme digestion. One of the clones with the 1.4 kb fragment inserted in the correct orientation was designated as FIX(-G)/pD2. *E. coli* RR1 transformed with FIX(-G)/pD2 has been deposited with ATCC under accession number 53067.

BHK cells were co-transfected with FIX(-G)/pD2 and pKO-neo as described above. Drug-resistant cells were selected and prepared for ELISA and activity assay as described in Example 6.

The assay for biological activity is based on the ability of Factor IX to reduce the clotting time of plasma from Factor IX-deficient patients to normal. It was done as described by Proctor and Rapaport (*Amer. J. Clin. Path.* 36: 212, 1961). Results are shown in Table 3.

TABLE 3

| Day | Cells/ml ($\times 10^{-4}$) | Factor IX polypeptide (ng/ml) supernatant | Factor IX polypeptide (ng/ml) pellet | Factor IX activity (ng/ml) in supernatant | % active protein in supernatant |
|---|---|---|---|---|---|
| 1 | 1.65 | — | — | — | — |
| 2 | 2.66 | 57 | 20 | 27 | 50% |
|   |   | 45 | 20 | 24 |   |
| 3 | 9.69 | 150 | 60 | 72 | 58% |
|   |   | 120 | 60 | 84 |   |
| 4 | 14.79 | 475 | 160 | 198 | 50% |
|   |   | 225 | 140 | 150 |   |
| 5 | 50.85 | 875 | 250 | 408 | 45% |
|   |   | 1000 | 260 | 438 |   |

The amount of Factor IX polypeptide was determined by ELISA essentially as described in Example 6 using polyclonal rabbit antisera to Factor IX. Following the incubation of the wells with the Factor IX-containing samples, the wells were rinsed and incubated 1 hour at room temperature with 200 ul of affinity purified rabbit polyclonal anti-Factor IX conjugated to alkaline phosphatase diluted 1:1000 in PBS containing 1% BSA and 0.05% Tween 20. The wells were then rinsed four times with PBS containing 0.05% Tween 20, and enzyme substrate was added as above. Incubations were run at 4° C. overnight or 37° C. for 2 hours.

As shown in Table 3, 70%-80% of the Factor IX polypeptide is secreted into the media, and about 50% of this is biologically active. No Factor IX activity was detected in the cell pellets.

Highest levels of activity were achieved by supplementing the cell culture medium with vitamin K (phytonadione, Merck) at concentrations of 1-10 µg/ml.

Several additional analyses were performed to demonstrate that the cells were secreting authentic Factor IX. Samples containing Factor IX activity according to the above assay were incubated with Factor VIII-deficient plasma but did not affect the clotting time, indicating that the activity was due to authentic Factor IX rather than a non-specific clotting agent. This conclusion was further verified by depletion of Factor IX activity from the samples with a specific antibody. Ninety-seven to ninety-eight percent of the Factor IX activity was immunoprecipitated from cell supernatants with a rabbit polyclonal antibody against Factor IX. This antibody also precipitated over 99% of the Factor IX activity from normal plasma. No Factor IX activity was removed from the supernatants by rabbit polyclonal antibody to erythropoietin.

Example 8

Construction of an Expression Vector for Factor VII

An expression vector comprising the synthetic Factor VII 5' coding region joined to the partial Factor VII cDNA was constructed. The vector, designated pM7135, was generated by inserting the Factor IX leader—5' Factor VII sequence from pM7115 and the 3' Factor VII sequence from FIX/VII/pD2 into plasmid pD3, which comprises the SV40 enhancer and the adenovirus 2 major late promoter and tripartite leader.

Plasmid pD3 was generated from plasmid pDHFRIII. The Pst I site immediately upstream from the DHFR sequence in pDHFRIII was converted to a Bcl I site by digesting 10 ug of plasmid with 5 units of Pst I for 10' at 37° C. in 100 ul buffer A (10 mM Tris pH 8, 10 mM $MgCl_2$, 6 mM NaCl, 7 mM β-MSH). The DNA was phenol extracted, EtOH precipitated, and resuspended in 40 ul buffer B (50 mM This pH 8, 7 mM $MgCl_2$, 7 mM β-MSH) containing 10 mM dCTP and 16 units T4 DNA polymerase and incubated at 12° C. for 60 minutes. Following EtOH precipitation, the DNA was ligated to 2.5 ug kinased Bcl I linkers in 14 ul buffer C (10 mM Tris pH 8, 10 mM $MgCl_2$, 1 mM DTT, 1.4 mM ATP) containing 400 units T4 polynucleotide ligase for 12 hours at 12° C. Following phenol extraction and EtOH precipitation, the DNA was resuspended in 120 ul buffer D (75 mM KCl, 6 mM Tris pH 7.5, 10 mM $MgCl_2$, 1 mM DTT), digested with 80 units Bcl I for 60 minutes at 50° C., then electrophoresed through agarose. Form III plasmid DNA (10 ug) was isolated from the gel, and ligated in 10 ul buffer C containing 50 units T4 polynucleotide ligase for 2 hours at 12° C., and used to transform *E. coli* HB101. Positive colonies were identified by rapid DNA preparation analysis, and plasmid DNA (designated pDHFR') prepared from positive colonies was transformed into dAM⁻ *E. coli*.

Plasmid pD2' was then generated by cleaving pDHFR' (15 ug) and pSV40 (25 ug) in 100 ul buffer D with 25 units Bcl I for 60 minutes at 50° C., followed by the addition of 50 units Bam HI and additional incubation at 37° C. for 60 minutes. DNA fragments were resolved by agarose gel electrophoresis, and the 4.9 kb pDHFR' fragment and 0.2 kb SV40 fragment were isolated. These fragments (200 ng pDHFR' DNA and 100 ng SV40 DNA) were incubated in 10 ul buffer C containing 100 units T4 polynucleotide ligase for 4 hours at 12° C., and the resulting construct (pD2') used to transform *E. coli* RRI.

Plasmid pD2' was modified by deleting the "poison" sequences in the pBR 322 region (Lusky and Botcham, *Nature* 293: 79-81, 1981). Plasmids pD2' (6.6 ug) and pML-1 (lusky and Botcham, ibid) (4 ug) were incubated in 50 ul buffer A with 10 units each Eco RI and Nru I for 2 hours at 37° C., followed by agarose gel electrophoresis. The 1.7 kb pD2' fragment and 1.8 kb pML fragment were isolated and ligated together (50 ng each) in 20 ul buffer C containing 100 units T4 polynucleotide ligase for 2 hours at 12° C., followed by transformation into *E. coli* HB101. Colonies containing the desired construct (designated Δ pD2) were identified by rapid preparation analysis. Ten ug of Δ pD2 were then digested with 20 units each Eco RI and Bgl II, in 50 ul buffer A for 2 hours at 37° C. The DNA was electrophoresed through agarose, and the desired 2.8 kb fragment (fragment C) comprising the pBR322, 3' splice site and poly A sequences was isolated.

To generate the remaining fragments used in constructing pD3, pDHFRIII was modified to convert the Sac II (Sst II) site into either a Hind III or Kpn I site. Ten ug pDHFRIII were digested with 20 units Sst II for 2 hours at 37° C., followed by phenol extraction and ethanol precipitation. Resuspended DNA was incubated in 100 ul buffer B containing 10 mM dCTP and 16 units T4 DNA polymerase for 60 minutes at 12° C., phenol extracted, dialyzed, and ethanol precipitated. DNA (5 ug) was ligated with 50 ng kinased Hind III or Kpn I linkers in 20 ul buffer C containing 400 units T4 DNA ligase for 10 hours at 12° C., phenol extracted, and ethanol precipitated. After resuspension in 50 ul buffer A, the resultant plasmids were digested with 50 units Hind III or Kpn I, as appropriate, and electrophoresed through agarose. Gel-isolated DNA (250 ng) was ligated in 30 ul buffer C containing 400 units T4 DNA ligase for 4 hours at 12° C. and used to transform *E. coli* RR1. The resultant plasmids were designated pDHFRIII (Hind III) and pDHFRIII (Kpn I). A 700 bp Kpn I-Bgl II fragment (fragment A) was then purified from pDHFRIII (Kpn I) by digestion with Bgl II and Kpn I followed by agarose gel electrophoresis.

The SV40 enhancer sequence was inserted into pDHFRIII (Hind III) as follows: 50 ug SV40 DNA was incubated in 120 ul buffer A with 50 units Hind III for 2 hours at 37° C., and the Hind III C SV40 fragment (5089-968 bp) was gel purified. Plasmid pDHFRIII (Hind III) (10 ug) was treated with 250 ng calf intestinal phosphatase for 1 hour at 37° C., phenol extracted and ethanol precipitated. The linearized plasmid (50 ng) was ligated with 250 ng Hind III C SV40 in 16 ul buffer C for 3 hours at 12° C., using 200 units T4 polynucleotide ligase, and transformed into *E. coli* HB101. A 700 base pair Eco RI-Kpn I fragment (fragment B) was then isolated from this plasmid.

For the final construction of pD3, fragments A and B (50 ng each) were ligated with 10 ng fragment C with 200 units T4 polynucleotide ligase for 4 hours at 12° C., followed by transfection of *E. coli* RR1. Positive colonies were detected by rapid preparation analysis, and a large-scale preparation of pD3 was made.

Figure 8:
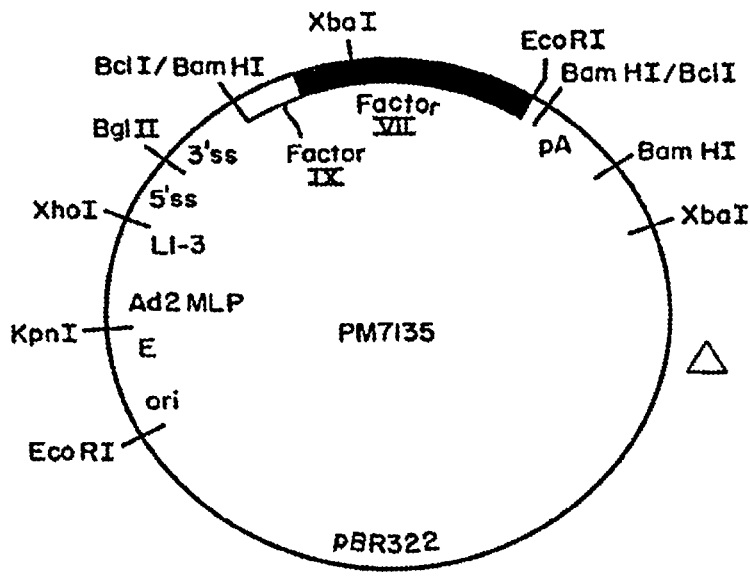
FIG. 8 illustrates expression vector pM7135. Symbols used are E, the SV40 enhancer; ori, the SV40 origin of replication; pA, the early polyadenylation signal from SV40; Δ, the deletion site of the pBR322 "poison" sequences; and other symbols as described for FIG. 6.

Expression vector pM7135 was then constructed. The replicative form of pM7115 was digested with Bam HI and Xba I and the 550 base pair fragment comprising the Factor IX leader and 5' Factor VII sequence was gel purified. Plasmid FIX/VII/pD2 was digested with Xba I and Bam HI and the 1700 bp fragment comprising the 3' portion of the Factor VII cDNA was gel purified. Plasmid pD3 was digested with Bcl I, treated with calf alkaline phosphatase, and the three fragments joined in a triple ligation. The resultant constructs were screened for the presence of a 2000 base pair Xba I fragment. A plasmid having the correct orientation was selected and designated pM7135 (FIG. 8). *E. coli* JM101 transformed with pM7135 has been deposited with American Type Culture Collection under accession number 53083.

From the foregoing it will be appreciated that, although specific embodiments of the invention have been described herein for purposes of illustration, various modifications may be made without deviating from the spirit and scope of the invention. Accordingly, the invention is not to be limited except as by the appended claims.

The invention claimed is:

1. Isolated mammalian cells stably transfected with an expression vector comprising a promoter operably linked to a DNA sequence encoding human Factor IX, wherein said cells produce active human Factor IX at a level of at least approximately 2.57 ng/$10^4$ cells/day.

2. Isolated mammalian cells stably transfected with a DNA construct containing a nucleotide sequence which codes at least partially for human Factor IX, said nucleotide sequence comprising a first nucleotide sequence encoding a leader peptide and gla domain, wherein both said gla domain and leader peptide are the gla domain and leader peptide of human Factor IX, said first nucleotide sequence joined to a second nucleotide sequence positioned downstream of said first sequence, said second sequence encoding the catalytic domain for the serine protease activity of human Factor IX, the joined sequences coding for a protein having the biological activity for blood coagulation of human Factor IX, wherein said cells produce said protein at a level of at least approximately 2.57 ng/10⁴ cells/day.

3. An in vitro method of producing a protein having a biological activity for blood coagulation mediated by Factor IX, comprising:

establishing a mammalian host cell which contains a DNA construct containing a nucleotide sequence which codes at least partially for human Factor IX, said nucleotide sequence comprising a first nucleotide sequence encoding a leader peptide and gla domain, wherein both said gla domain and leader peptide are the gla domain and leader peptide of a human Factor IX, said first nucleotide sequence joined to a second nucleotide sequence positioned downstream of said first sequence, said second sequence encoding the catalytic domain for the serine protease activity of human Factor IX, the joined sequences coding for a protein which, upon activation, has the biological activity for blood coagulation of human Factor IX, at a level of at least approximately 2.57 ng/10⁴ cells/day;

growing said mammalian host cell in an appropriate medium; and isolating the protein product encoded by said DNA construct produced by said mammalian host cell.

4. The method of claim 3, wherein the step of establishing includes amplification of the joined sequences by cotransfection of the host cell with a gene encoding dihydrofolate reductase, wherein the appropriate medium comprises methotrexate.

5. The method of claim 3 wherein said medium contains vitamin K.

6. The stably transfected mammalian cells of claim 1 which are baby hamster kidney cells.

* * * * *